United States Patent
Cassinis

(10) Patent No.: US 10,285,774 B2
(45) Date of Patent: May 14, 2019

(54) MEDICAL KIT AND DISPENSER FOR MEDICAL KITS

(71) Applicant: Certol International LLC, Commerce City, CO (US)

(72) Inventor: Edward A. Cassinis, Highlands Ranch, CO (US)

(73) Assignee: Certol International LLC, Commerce City, CO (US)

( * ) Notice: Subject to any disclaimer, the term of this patent is extended or adjusted under 35 U.S.C. 154(b) by 0 days.

(21) Appl. No.: 16/017,127

(22) Filed: Jun. 25, 2018

(65) Prior Publication Data

US 2019/0083199 A1 Mar. 21, 2019

Related U.S. Application Data

(60) Provisional application No. 62/559,737, filed on Sep. 18, 2017.

(51) Int. Cl.
*B65D 69/00* (2006.01)
*B65D 81/20* (2006.01)
(Continued)

(52) U.S. Cl.
CPC .............. *A61B 90/70* (2016.02); *A61B 50/30* (2016.02); *A61B 2050/3007* (2016.02);
(Continued)

(58) Field of Classification Search
CPC .. B65D 31/04; B65D 75/002; B65D 81/2023; A61B 31/04; A61B 75/002; A61B 81/2023
(Continued)

(56) References Cited

U.S. PATENT DOCUMENTS 3,367,785 A * 2/1968 Finucane ............... A21D 15/00
206/219
3,374,882 A 3/1968 Amaliksen
(Continued)

FOREIGN PATENT DOCUMENTS

WO WO-2004-035406 A1 4/2004

OTHER PUBLICATIONS

HMB Endoscopy Products (Jul. 2017) "Endoscope Cleaning Products, Olympus Pentax Fujinon Scope Cleaning Kits," available web site: https://www.hmbendoscopy.com/endoscope-cleaning-products.html; accessed on Jul. 18, 2017, 2 pages.
(Continued)

*Primary Examiner* — Luan K Bui
(74) *Attorney, Agent, or Firm* — Adsero IP

(57) ABSTRACT

Novel tools and techniques are provided for implementing a medical kit, and, more particularly, to methods, systems, and apparatuses for implementing a medical kit for cleaning endoscopes. In some aspects, a medical kit may comprise an outer bag capable of being vacuum sealed, at least one inner bag contained within the outer bag, at least one solution container comprising a solution contained within the outer bag, at least one absorbent pad contained within the outer bag, and/or the like. The air from the outer bag may be evacuated to form a vacuum seal surrounding the at least one inner bag, the at least one solution container, and the at least one absorbent pad. In an additional aspect, the medical kit may comprise an absorbent pad and solution contained within a bag capable of being vacuum sealed. In yet another aspect, a dispenser may be implemented to dispense medical kits.

10 Claims, 21 Drawing Sheets

(51) Int. Cl.
  *A61B 90/70* (2016.01)
  *A61B 50/30* (2016.01)
  B65D 30/08 (2006.01)
  B65D 75/00 (2006.01)

(52) U.S. Cl.
  CPC ... *A61B 2050/316* (2016.02); *A61B 2090/701* (2016.02); *A61L 2202/24* (2013.01); *B65D 31/04* (2013.01); *B65D 75/002* (2013.01)

(58) Field of Classification Search
  USPC .... 206/205, 210, 438, 524.8, 570, 572, 803; 221/45, 52
  See application file for complete search history.

(56) References Cited

U.S. PATENT DOCUMENTS

| | | | |
|---|---|---|---|
| 3,747,802 A * | 7/1973 | Uroshevich | B65D 43/162 |
| | | | 206/494 |
| 3,802,555 A | 4/1974 | Grasty et al. | |
| 3,815,315 A * | 6/1974 | Glick | A61B 17/06133 |
| | | | 206/210 |
| 4,295,566 A * | 10/1981 | Vincek | A61L 2/28 |
| | | | 116/266 |
| 4,989,733 A | 2/1991 | Patry | |
| 5,152,394 A | 10/1992 | Hughes | |
| 5,988,371 A | 11/1999 | Paley et al. | |
| 6,006,917 A | 12/1999 | Loeffler | |
| 6,068,820 A | 5/2000 | De Guzman | |
| 6,176,067 B1 | 1/2001 | Bahten | |
| 6,439,386 B1 * | 8/2002 | Sauer | B65D 5/4208 |
| | | | 206/494 |
| 7,147,129 B1 * | 12/2006 | Menefield | A61F 6/005 |
| | | | 221/283 |
| 7,178,312 B2 | 2/2007 | Snell | |
| 8,925,115 B1 | 1/2015 | Hanna et al. | |
| 2003/0029740 A1 | 2/2003 | Caveness | |
| 2003/0128899 A1 | 7/2003 | Dennis | |
| 2004/0000503 A1 * | 1/2004 | Shah | B65D 33/01 |
| | | | 206/524.8 |
| 2004/0031721 A1 | 2/2004 | Mann | |
| 2004/0172002 A1 | 9/2004 | Nelson et al. | |
| 2005/0143706 A1 | 6/2005 | Snell | |
| 2005/0189372 A1 | 9/2005 | Fenton | |
| 2008/0147035 A1 | 6/2008 | Snell | |
| 2009/0200198 A1 * | 8/2009 | Guelzow | A61F 2/0095 |
| | | | 206/570 |
| 2010/0065445 A1 | 3/2010 | Stevenson | |
| 2010/0323069 A1 | 12/2010 | Rubinstein | |
| 2012/0047850 A1 | 3/2012 | Kemp et al. | |
| 2012/0124943 A1 | 5/2012 | Nakamura et al. | |
| 2013/0037440 A1 * | 2/2013 | Danchisin | A61K 8/66 |
| | | | 206/570 |
| 2014/0117013 A1 | 5/2014 | Macler | |
| 2014/0217112 A1 * | 8/2014 | Young | A47K 10/425 |
| | | | 221/45 |
| 2015/0060323 A1 | 3/2015 | Welch et al. | |
| 2015/0329274 A1 | 11/2015 | Bennett et al. | |

OTHER PUBLICATIONS

Cygnus Medical (Jul. 2017) "Endoscopy | Manual Cleaning—Bedside | First Step Flexible Endoscope Bedside Pre-Clean Kits," available web site: http://www.cygnusmedical.com/products/first_step/fs.html accessed on Jul. 18, 2017, 3 pages.
International Search Report and Written Opinion prepared by the Korean International Property office as International Searching Authority for PCT International Patent Application No. PCT/US2018/050493, dated Jan. 31, 2019, 14 pages.
U.S. Appl. No. 16/017,001, Office Action dated Mar. 22, 2019, 15 pages.
U.S. Appl. No. 16/017,047, Office Action dated Mar. 22, 2019, 15 pages.

* cited by examiner

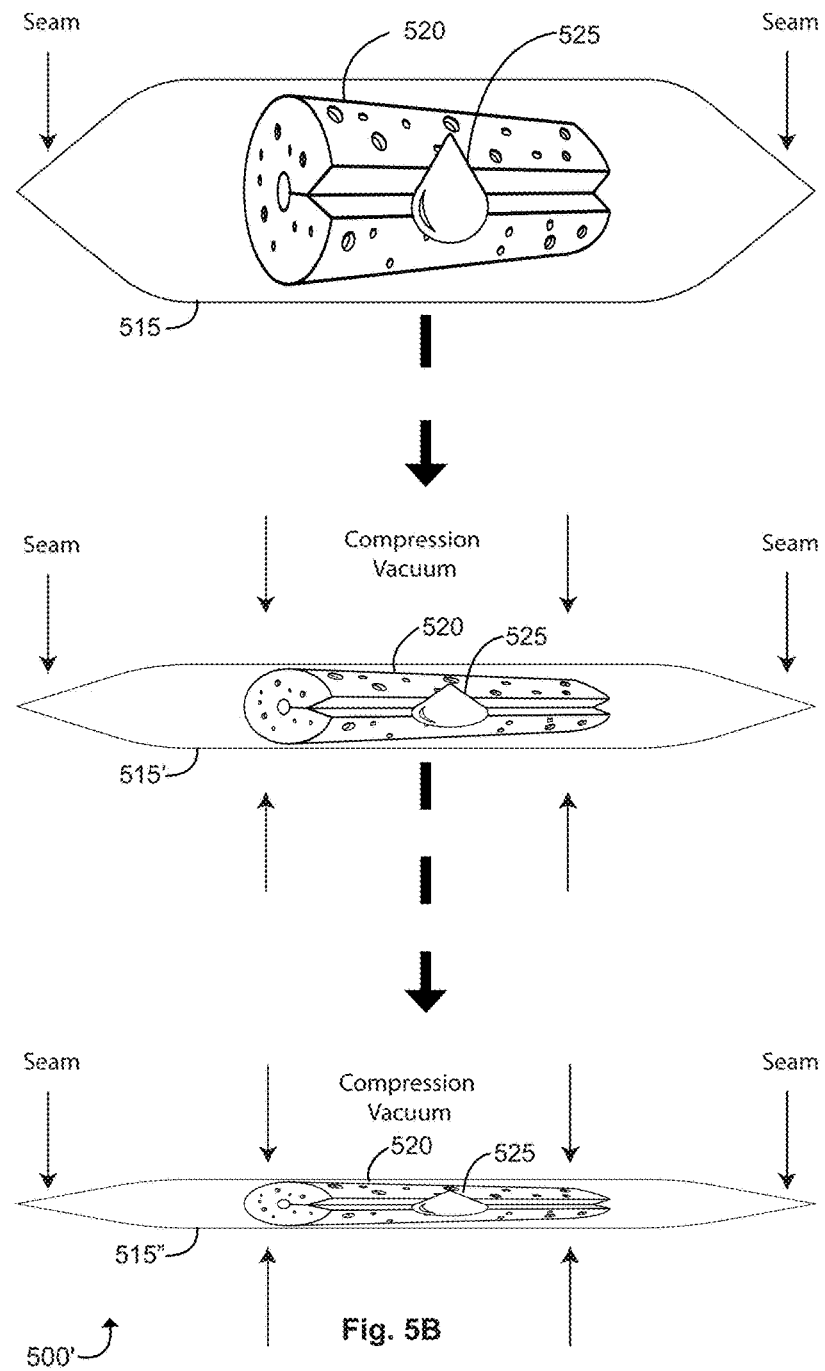

MEDICAL KIT AND DISPENSER FOR MEDICAL KITS

CROSS-REFERENCES TO RELATED APPLICATIONS

This application claims priority to U.S. Patent Application Ser. No. 62/559,737 (the "'737 Application"), filed on Sep. 18, 2017, by Edward A. Cassinis, entitled, "Medical Kit and Dispenser for Medical Kits," the disclosure of which is incorporated herein by reference in its entirety for all purposes.

This application may be related to each of U.S. patent application Ser. No. 16/017,001 (the "'001 Application"), filed Jun. 25, 2018 by Edward A. Cassinis, entitled, "Medical Kit and Dispenser for Medical Kits," and U.S. patent application Ser. No. 16/017,047 (the "'047 Application"), filed Jun. 25, 2018 by Edward A. Cassinis, entitled, "Medical Kit and Dispenser for Medical Kits."

The respective disclosures of these applications/patents (which this document refers to collectively as the "Related Applications") are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, and apparatuses for implementing a medical kit, and, more particularly, to methods, systems, and apparatuses for implementing a medical kit for cleaning endoscopes.

BACKGROUND

While a variety of medical kits exist in the medical and dental markets, these medical kits can be bulky and take up a lot of space. Hospitals, medical offices, dental offices, and the like often have limited storage space with which to store the medical kits. Thus, hospitals, medical offices, dental offices, and the like may only have a limited number of medical kits stored onsite and may have to frequently order additional medical kits from a supplier. Bulky medical kits also add to shipping and handling costs. Further, it is desirable to ensure that an entire medical kit is sterile and ready for use in an intensive care unit, operating room, and/or the like.

Various medical kits on the market comprise a bag containing solution and an absorbent pad. The absorbent pad may be in fluid contact with the solution and may at least partially absorb the solution contained within the bag. In addition to the absorbent pad and solution, the medical kits also comprise a significant amount of air. The absorbent pad in fluid contact with the solution and the air in the medical kits cause the medical kits to be bulky and take up space.

Hence, there is a need for more robust and scalable solutions for implementing a medical kit, and, more particularly, for implementing a medical kit for cleaning endoscopes.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 5A and 5B are schematic diagrams illustrating a vacuum sealing process for vacuum sealing one or more medical kits, in accordance with various embodiments.

DETAILED DESCRIPTION OF CERTAIN EMBODIMENTS

Overview

Figure 1A:
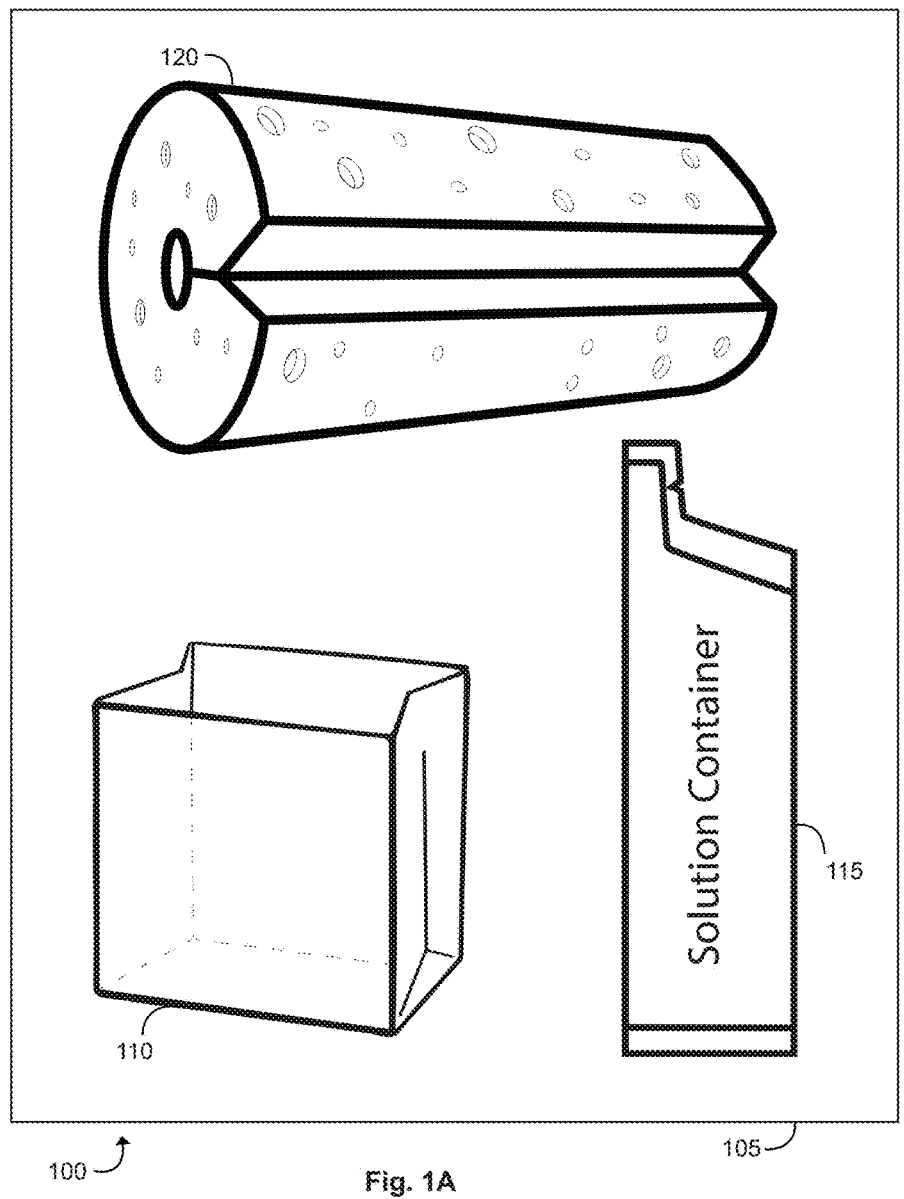
FIGS. 1A-1D are schematic diagrams illustrating a medical kit, in accordance with various embodiments.

Various embodiments provide improved techniques for implementing a medical kit, and, more particularly, to methods, systems, and apparatuses for implementing a medical kit for cleaning endoscopes.

In various embodiments, a medical kit (which may include medical kits and/or dental kits) might comprise an outer bag that is capable of being vacuum sealed. The outer bag may contain at least one inner bag, at least one solution container comprising a solution contained within the outer bag, and at least one absorbent pad contained within the outer bag. The outer bag may then be evacuated to form a vacuum seal surrounding the at least one inner bag, the at least one solution container, and the at least one absorbent pad.

In various other embodiments, a medical kit (which may include medical kits and/or dental kits) might comprise a bag that is capable of being vacuum sealed. The bag may contain at least one absorbent pad and a solution in fluid communication with the at least one absorbent pad. The bag may then be evacuated to form at least a partial vacuum seal surrounding the at least one absorbent pad and the solution in fluid communication with the at least one absorbent pad.

According to additional embodiments, a dispenser for dispensing medical kits may be provided. The dispenser may comprise a container. The container may have a top, a bottom, and a body between the top and the bottom. A plurality of medical kits may be disposable within the body of the container. Each medical kit may comprise an outer bag containing at least one inner bag, at least one solution container, and at least one absorbent pad. The outer bag may be evacuated to form a vacuum seal surrounding the at least one inner bag, the at least one solution container, and the at least one absorbent pad. Additionally, and/or alternatively, each medical kit (which may include medical kits and/or dental kits) might comprise a bag that is capable of being vacuum sealed. The bag may contain at least one absorbent pad and a solution in fluid communication with the at least one absorbent pad. The bag may then be at least partially evacuated to form at least a partial vacuum seal surrounding the at least one absorbent pad and the solution in fluid communication with the at least one absorbent pad. A lid may be attached to the container of the medical dispenser and an opening may be disposed near the bottom of the container. The opening disposed near the bottom of the container may be configured to dispense at least one medical kit at a time from the bottom of the container.

In this manner, medical kits (which may include both medical kits and dental kits) can be more easily stored in hospitals, medical offices, dental offices, warehouses, and/or the like. Further, by vacuum sealing the medical kit within a protective bag and/or layer, the contents of the medical kit may be maintained in a sterile environment. This allows doctors, dentists, nurses, medical practitioners, dental practitioners, and/or the like to immediately use the medical kit in an intensive care unit, operating room, and/or the like without having to sterilize the medical kit first.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

In an aspect, a medical kit might comprise an outer bag capable of being vacuum sealed, at least one inner bag contained within the outer bag, at least one solution container comprising a solution contained within the outer bag, and at least one absorbent pad contained within the outer bag. The outer bag may be evacuated to form a vacuum seal surrounding the at least one inner bag, the at least one solution container, and the at least one absorbent pad. By evacuating air from the outer bag, the size of the outer bag and the size of the contents inside the outer bag may be reduced. In some embodiments, the medical kit may be configured for use as an endoscope cleaning kit. The endoscope may be at least one of a cystoscope, a nephroscope, a bronchoscope, an arthroscope, a colonoscope, or a laparoscope, and/or the like.

The at least one inner bag, the at least one solution container, and the at least one absorbent pad may be sterilized and maintained within a sterile environment within the vacuum sealed outer bag. The vacuum sealing of the medical kit may be conducted in a sterile environment such that the contents of the medical kit remain sterile until the outer bag is opened. Alternatively, the contents of the medical kit may be sterilized after vacuum sealing the medical kit. This may be done by irradiating the medical kit after it is vacuum packed. Thus, the contents of the outer bag may be used immediately in sterile areas such as operating rooms, intensive care units, and/or the like. In order to maintain the sterile environment within the vacuum sealed outer bag, the outer bag may be sealed with at least one of glue, tape, compression, thermosetting, adhesive-curing, or melting an end of the outer bag, and/or the like.

The at least one inner bag may be used by a doctor, dentist, medical practitioner, or dental practitioner, and/or the like, to house components (e.g., the solution, absorbent pad, and/or the like) when the outer bag is opened. A user of the medical kit may mix solutions within the inner bag and/or place an absorbent pad in the inner bag with the solution, mixture of solution, and/or the like.

The at least one inner bag may be arranged within the outer bag such that, when the outer bag is opened, the inner bag does not rip or tear. The at least one inner bag may be empty and/or unsealed. The at least one inner bag may be configured to stand upright when unfolded. The at least one inner bag may further comprise at least two sidewall panels. The side wall panels of the at least one inner bag may be configured to expand. By having the side wall panels of the at least one inner bag expand, a user of the medical kit can easily insert his/her hand into the inner bag. The medical kit may further comprise at least two inner bags. Each inner bag of the at least two inner bags may be used for a different purpose. Further, the at least two inner bags may be different sizes.

In additional embodiments, the solution contained within the solution container may be at least one of a cleaning solution, a detergent, a ready-to-use detergent, a concentrated detergent, a ready-to-use enzymatic detergent, a concentrated enzymatic detergent, water, distilled water, desalinated water, sterilized water, deionized water, sterilized distilled water, sterilized desalinated water, sterilized deionized water, and/or the like. The medical kit may further comprise at least two solution containers. The at least two solution containers may comprise at least two different solutions. A user of the medical kit may be able to mix the at least two different solutions in the inner bag.

The absorbent pad contained in the outer bag may be at least one of a cloth, a sponge, a textured sponge, a square sponge, or a tubular sponge, and/or the like. In use and once the outer bag is opened, the absorbent pad may be placed in fluid contact with the solution in the inner bag.

The medical kit may further comprise at least one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, one or more biohazard stickers, one or more bags containing water, or one or more valves (e.g., one or more air/water valves, one or more suction valves, one or more biopsy valves), and/or the like. Additionally, and/or alternatively, the medical kit may comprise at least one of a plurality of pairs of gloves of different sizes, a plurality of transport bags of different sizes, a plurality of masks of different sizes, a plurality of nasal cannulas of different sizes, a plurality of tip guards of different sizes, or a plurality of brushes of different sizes, and/or the like.

In another aspect, a method might comprise providing a first layer of vacuum sealable material, providing a plurality of medical kits, wherein each medical kit comprises at least one inner bag, at least one solution container, and at least one absorbent pad, placing at least two medical kits of the plurality of medical kits in at least two different places on top of the first layer of vacuum sealable material, placing a second layer of vacuum sealable material over the first layer of vacuum sealable material and the at least two medical kits, creating at least two chambers with the first layer of vacuum sealable material and the second layer of vacuum sealable material, wherein each chamber contains one medical kit, and vacuum sealing each of the at least two chambers.

In additional embodiments, the at least two chambers may be attached to one another. This attachment may be a removable attachment. The at least two chambers may be attached to one another via one or more perforations between each chamber. The at least two chambers may be detachable from one another via the one or more perforations between each chamber. The at least two chambers may be configured to be stacked on top of each other.

Additionally, and/or alternatively, the at least two chambers may be configured to be attached to one another via at least one of a string, a strip of plastic, or tape, and/or the like. When the at least two chambers are attached to one another via at least one of the string, the strip of plastic, or the tape, and/or the like, the at least two chambers may be configured to stand upright on edges corresponding to the at least two chambers. The at least two chambers may further be stored by attaching a specified number of chambers together and placing the specified number of chambers upright on edges corresponding to the specified number of chambers.

Each chamber may comprise one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, one or more biohazard stickers, one or more bags containing water, or one or more valves (e.g., one or more air/water valves, one or more suction valves, one or more biopsy valves), and/or the like. Additionally, and/or alternatively, each chamber of the plurality of chambers may further comprise at least one of a plurality of pairs of gloves of different sizes, a plurality of transport bags of different sizes, a plurality of masks of different sizes, a plurality of nasal cannulas of different sizes, a plurality of tip guards of different sizes, or a plurality of brushes of different sizes, and/or the like.

In an additional aspect, a medical kit may comprise a first bag capable of being vacuum sealed, at least one absorbent pad contained within the first bag, and a solution contained within the first bag and in contact with the at least one absorbent pad. The first bag may be partially evacuated to form at least a partial vacuum seal surrounding the at least one absorbent pad and the solution. By, at least partially, evacuating air from the bag, the size of the bag and the size of the contents inside the first bag may be reduced. In some embodiments, the medical kit may be configured for use as an endoscope cleaning kit. The endoscope may be at least one of a cystoscope, a nephroscope, a bronchoscope, an arthroscope, a colonoscope, or a laparoscope, and/or the like.

The at least one absorbent pad and the solution contained within the first bag and in contact with the at least one absorbent pad may be sterilized and maintained within a sterile environment within the at least partially vacuum sealed bag. The vacuum sealing of the medical kit may be conducted in a sterile environment such that the contents of the medical kit remain sterile until the first bag is opened. Alternatively, the contents of the medical kit may be sterilized after vacuum sealing the medical kit. This may be done by irradiating the medical kit after it is vacuum packed. Thus, the contents of the first bag may be used immediately in sterile areas such as operating rooms, intensive care units, and/or the like. In order to maintain the sterile environment within the vacuum sealed first bag, the first bag may be sealed with at least one of glue, tape, compression, thermo-setting, adhesive-curing, or melting an end of the bag, and/or the like.

The medical kit may further comprise an outer bag surrounding the partially vacuum sealed first bag. The outer bag may be evacuated to form a vacuum seal surrounding the first bag.

The solution contained within the first bag may be at least one of a cleaning solution, a detergent, a ready-to-use detergent, a concentrated detergent, a ready-to-use enzymatic detergent, a concentrated enzymatic detergent, water, distilled water, desalinated water, sterilized water, deionized water, sterilized distilled water, sterilized desalinated water, sterilized deionized water, and/or the like. The medical kit may comprise at least two different solutions.

The medical kit may further comprise, within the outer bag and outside of the first bag, at least one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, one or more biohazard stickers, one or more bags containing water, or one or more valves (e.g., one or more air/water valves, one or more suction valves, one or more biopsy valves), and/or the like. Additionally, and/or alternatively, the medical kit may further comprise, within the outer bag and outside of the first bag, at least one of a plurality of pairs of gloves of different sizes, a plurality of transport bags of different sizes, a plurality of masks of different sizes, a plurality of nasal cannulas of different sizes, a plurality of tip guards of different sizes, or a plurality of brushes of different sizes, and/or the like. The outer bag may be vacuum sealed to surround the first bag and at least one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, one or more biohazard stickers, one or more bags containing water, one or more valves (e.g., one or more air/water valves, one or more suction valves, one or more biopsy valves), and/or the like.

In another aspect, a method for making a medical kit may comprise providing a bag capable of being vacuum sealed, placing at least one absorbent pad within the bag, placing a solution on the absorbent pad contained within the bag, wherein the solution is at least partially absorbed by the absorbent pad, and evacuating air from the bag to create a partial vacuum seal surrounding the at least one absorbent pad and the solution contained within the bag.

In yet another aspect, a method for making a medical kit may comprise providing a first layer of vacuum sealable material, placing at least one absorbent pad on top of the first layer of vacuum sealable material, placing a solution on the absorbent pad, wherein the solution is at least partially absorbed by the absorbent pad, and placing a second layer of vacuum sealable material over the first layer of vacuum sealable material, the at least one absorbent pad, and the solution. The method may further comprise creating at least one chamber with the first layer of vacuum sealable material and the second layer of vacuum sealable material, wherein each chamber contains the at least one absorbent pad and the solution, and evacuating air from the bag to create a partial vacuum seal surrounding the at least one absorbent pad and the solution contained within the bag.

In additional embodiments, the at least two chambers may be attached to one another. This attachment may be a removable attachment. The at least two chambers may be attached to one another via one or more perforations between each chamber. The at least two chambers may be detachable from one another via the one or more perforations between each chamber. The at least two chambers may be configured to be stacked on top of each other.

Additionally, and/or alternatively, the at least two chambers may be configured to be attached to one another via at least one of a string, a strip of plastic, or tape, and/or the like. When the at least two chambers are attached to one another via at least one of the string, the strip of plastic, or the tape, and/or the like, the at least two chambers may be configured to stand upright on edges corresponding to the at least two chambers. The at least two chambers may further be stored by attaching a specified number of chambers together and placing the specified number of chambers upright on edges corresponding to the specified number of chambers.

In some additional embodiments, the method might further comprise surrounding the at least one chamber with an outer bag and evacuating the outer bag to form a vacuum seal surrounding the at least one chamber. Additional items may be placed, within the vacuum sealed outer bag and outside of the vacuums sealed at least one chamber, including at least one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, one or more biohazard stickers, one or more bags containing water, or one or more valves (e.g., one or more air/water valves, one or more suction valves, one or more biopsy valves), and/or the like.

In yet another aspect, a dispenser for dispensing medical kits may be provided. The dispenser may comprise a container comprising a top, a bottom, and a body between the top and the bottom. A plurality of medical kits may be disposable within the body of the container. Each medical kit may comprise one outer bag containing at least one inner bag, at least one solution container, and at least one absorbent pad. The outer bag may be evacuated to form a vacuum seal surrounding the at least one inner bag, the at least one solution container, and the at least one absorbent pad. A lid may be attached to the top of the container and an opening may be disposed near the bottom of the container. The opening may be configured to dispense at least one medical kit at a time from the bottom of the container.

In another embodiment of the dispenser, the at least one medical kit may protrude slightly from the opening of the container. Additionally, and/or alternatively, removing the at least one medical kit protruding from the opening of the container may cause another at least one medical kit to protrude from the opening of the container.

The plurality of medical kits may be removably attached together via perforations. In order to remove the medical kits attached together via perforations, the bottom of the dispenser may comprise at least four spring loaded tabs and a hand tab on either side of the body near the bottom. The plurality of medical kits when disposed in the body may be arranged such that the perforations are adjacent to the sides of the dispenser. Removing one of the at least one medical kit by pulling a non-perforated side of the medical kit via one of the hand tabs may cause the spring-loaded tabs to flex and rebound to prevent the next medical kit from falling. The resultant hanging medical kit may then be removed by tearing along the perforations. The bottom of the container may be configured to aid a user in tearing the one or more medical kits along the perforations.

In additional embodiments, the bottom portion of the container may be slanted. Additionally, and/or alternatively, gravity may be used to aid dispensing of each medical kit from the container. The lid may be hingedly connected to the top of the container and the container may contain a predetermined amount of medical kits.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Specific Exemplary Embodiments

We now turn to the embodiments as illustrated by the drawings. FIGS. 1-10 illustrate some of the features of a method, system, and/or apparatus a medical kit, and, more particularly, to methods, systems, and apparatuses for implementing a medical kit for cleaning endoscopes, as referred to above. The methods, systems, and/or apparatuses illustrated by FIGS. 1-10 refer to examples of different embodiments that include various components and steps, which can be considered alternatives or which can be used in conjunction with one another in the various embodiments. The description of the illustrated methods, systems, and apparatuses shown in FIGS. 1-10 is provided for purposes of illustration and should not be considered to limit the scope of the different embodiments.

With reference to the figures, FIGS. 1A-1D (collectively, "FIG. 1") are schematic diagrams illustrating a medical kit 100, in accordance with various embodiments. The medical kit 100 may be a medical kit or a dental kit for use in a hospital, medical office, dental office, and/or the like. The medical kit 100 may be used for cleaning medical instruments such as surgical instruments, medical instruments, dental instruments, and/or the like. The medical kit 100 may also be used to clean endoscopes such as cystoscopes, nephroscopes, bronchoscopes, arthroscopes, colonoscopes, laparoscopes, and/or the like. It should be noted that the components depicted in FIG. 1 are not necessarily shown to scale, and can each be any suitable size consistent with the various embodiments described herein.

The medical kit 100 may comprise an outer bag 105. The outer bag 105 may be a bag that is capable of being vacuum sealed. The outer bag 105 may be vacuum sealed around components of the medical kit 100 to reduce the size of medical kit 100 and make it easier to store medical kit 100. Further, the vacuum sealing of the outer bag 105 may create a sterile environment within medical kit 100 such that the components of medical kit 100 may be immediately used in an operating room, intensive care unit, and/or the like.

Additionally, and/or alternatively, the outer bag 105 may comprise at least two layers. The at least two layers of the outer bag 105 may be attached together and surround components of the medical kit 100. The at least two layers of the outer bag 105 may be held together via glue, tape, compression, thermosetting, adhesive-curing, melting an end of at least one layer, and/or the like. The at least two layers of the outer bag 105 may also be vacuum sealable.

In some embodiments, a first layer of the at least two layers the outer bag 105 may be formed from at least one of a flexible or rigid film, a flexible or rigid plastic, or foam, and/or the like. The first layer may be formed to be a thin sheet of material, a tray, and/or the like. A second layer of the at least two layers of the outer bag 105 may be formed from at least one of a flexible or rigid film, a flexible or rigid plastic, or foam, and/or the like.

In another non-limiting example, a first layer may be made from foam and/or rigid plastic. The foam and/or rigid plastic may be formed in the shape of a tray. Contents of the medical kit 100 may be placed in the tray (on top of the first layer of material). A flexible film or flexible plastic (second layer) may be placed over the tray layer). When the air is evacuated from outer bag 105, the flexible film or flexible plastic (second layer) may be configured to surround the contents of the tray (first layer) and seal the contents between the tray (first layer) and the flexible film or flexible plastic (second layer).

Once the air from the outer bag 105 is evacuated, the outer bag may be sealed to maintain the vacuum within the outer bag with at least one of glue, tape, compression, thermosetting, adhesive-curing, or melting an end of the outer bag, and/or the like. The outer bag 105 may be made of water and/or liquid-impermeable material such as plastic, film, and/or the like.

The medical kit 100 may further comprise at least one inner bag 110. The at least one inner bag 110 may be arranged within the outer bag 105 such that when the outer bag 105 is opened, the inner bag 110 does not rip or tear. The at least one inner bag 110 may be empty (i.e., not containing any other components of the medical kit). Additionally, and/or alternatively, the inner bag 110 may contain at least one other component (e.g., an absorbent pad, solution, gloves, mask, etc.) of the medical kit 100.

The at least one inner bag 110 may also be unsealed within the outer bag 105. By having an unsealed inner bag 110, the inner bag 110 may easily be compressed when air from the outer bag 105 is evacuated. The inner bag 110 may be sterilized before being placed in outer bag 105.

The inner bag 110 may also be capable of being sealed. The seal of the inner bag 110 may be resealable and may be at least one of a press seal, a zip seal, or the like. The inner bag 110, being capable of being resealable, may be used to dispose of used components of the medical kit 100 without contaminating the intensive care unit, operating room, and/or the like.

The inner bag 110 may be used by a doctor, dentist, nurse, medical practitioner, or dental practitioner, and/or the like, to mix various components of the medical kit 100 after the medical kit 100 has been opened. In a non-limiting example, the at least one inner bag 110 may be used to contain a solution and at least one absorbent pad after the medical kit 100 is opened. The inner bag 110 may be made of water and/or liquid-impermeable material such as plastic, film, and/or the like such that liquid contained within the inner bag does not leak.

The inner bag 110 may be configured to stand upright when it is unfolded. In order to achieve this feature, the inner bag 110 may have a flat bottom, a bottom gusset panel, and/or the like. Additionally, and/or alternatively, the inner bag 110 may be configured to expand. In order to expand, the inner bag 110 may comprise at least two sidewall panels and the side wall panels may be configured to expand.

The inner bag 110 may further contain hash marks, gradation lines, and/or the like. The hash marks, gradation lines, and/or the like, may be located on a side panel, front panel, and/or back panel of the inner bag 110. The hash marks, gradation lines, and/or the like, may be used to indicate a measurement or a location indicating where to fill the inner bag 110 with solution.

The medical kit 100 may further comprise at least two inner bags 110. The at least two inner bags 110 may be of different sizes and/or may be used for different purposes.

Additionally, and/or alternatively, the medical kit 100 may comprise a solution contained within a solution container 115. The solution container 115 may contain a predetermined amount of solution that is needed for a particular task. By providing a predetermined amount of solution suitable for a particular task, a doctor, dentist, nurse, medical practitioner, or dental practitioner, and/or the like, does not need to measure out a particular amount of solution before using medical kit 100.

The solution contained within the solution container 115 may be at least one of a cleaning solution, a detergent, a ready-to-use detergent, a concentrated detergent, a ready-to-use enzymatic detergent, a concentrated enzymatic detergent, water, distilled water, desalinated water, sterilized water, deionized water, sterilized distilled water, sterilized desalinated water, or sterilized deionized water, and/or the like. The medical kit 100 may further contain at least two solution containers 115. The solutions contained within the at least two solution containers 115 may contain the same solution or at least two different solutions.

In a non-limiting example, the medical kit 100 may comprise a first solution container comprising a solution (e.g., a cleaning solution, a detergent, a ready-to-use detergent, a concentrated detergent, a ready-to-use enzymatic detergent, a concentrated enzymatic detergent, and/or the like) which needs to be diluted and a second solution container comprising a solution (e.g., water, distilled water, desalinated water, sterilized water, deionized water, sterilized distilled water, sterilized desalinated water, sterilized deionized water, and/or the like) that may be used to dilute the first solution. In an additional non-limiting example, the first solution container may comprise concentrated enzymatic detergent and the second container may comprise distilled water. By providing a concentrated enzymatic detergent, the shelf life of the medical kit may be expanded. Further, it is often difficult to find distilled/desalinated/deionized water in a hospital, medical office, dental office, and/or the like. By providing both the concentrated enzymatic detergent and the distilled/desalinated/deionized water, a doctor, dentist, nurse, medical practitioner, or dental practitioner, and/or the like, can easily mix the concentrated enzymatic detergent and distilled water onsite within inner bag 110.

The solution container 115 may be sterilized and vacuum sealed within outer bag 105.

The medical kit 100 may further comprise at least one absorbent pad 120. The absorbent pad 120 may be at least one of a cloth, a sponge, a textured sponge, a square sponge, or a tubular sponge, and/or the like. The absorbent pad 120 may be used (after the medical kit 100 is opened) to absorb the solution from the solution container 115 in the inner bag 110 and the absorbent pad 120 may be used to clean a medical instrument.

The absorbent pad 120 may be sterilized and vacuum sealed within outer bag 105.

Figure 1B:
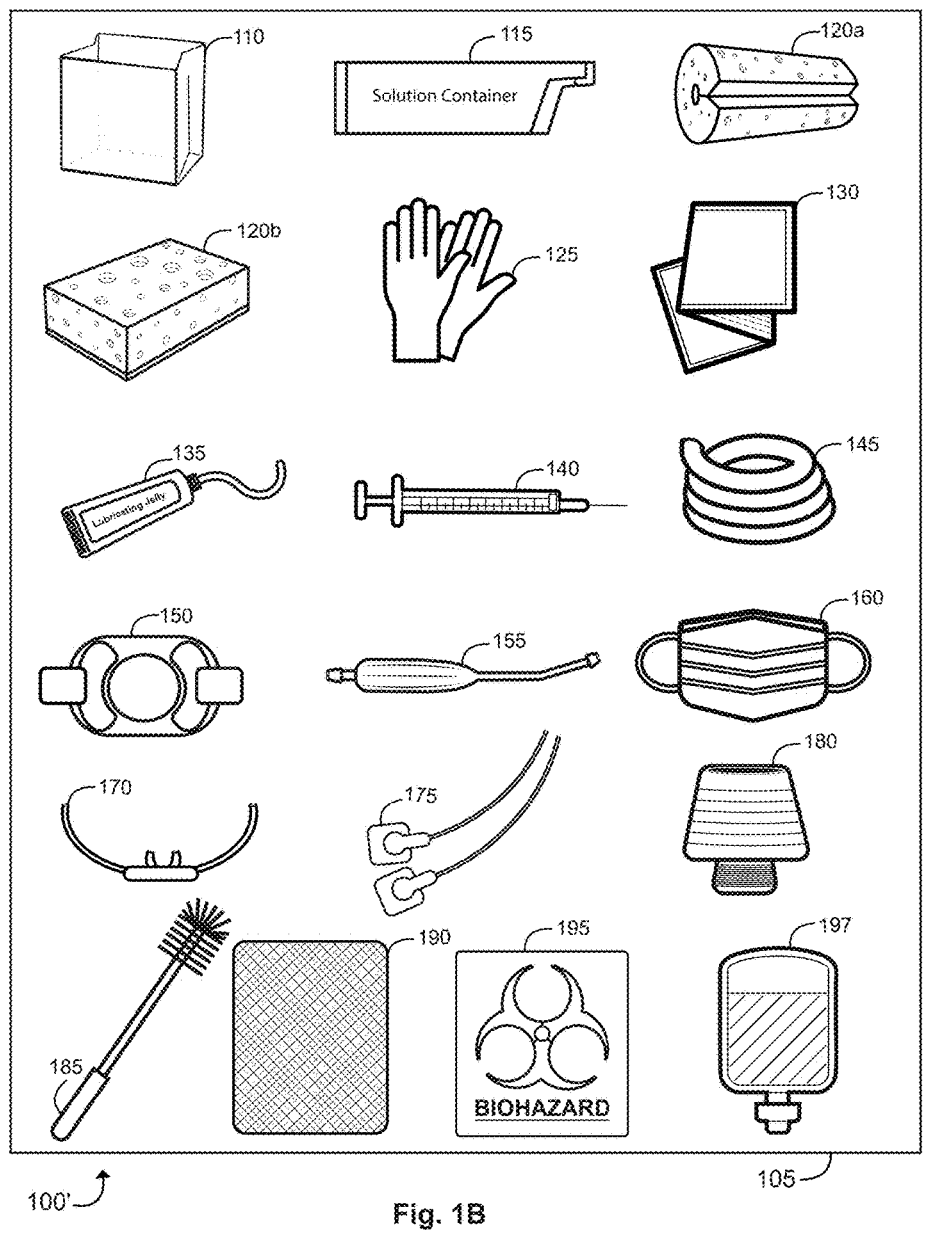
Figure 1C:
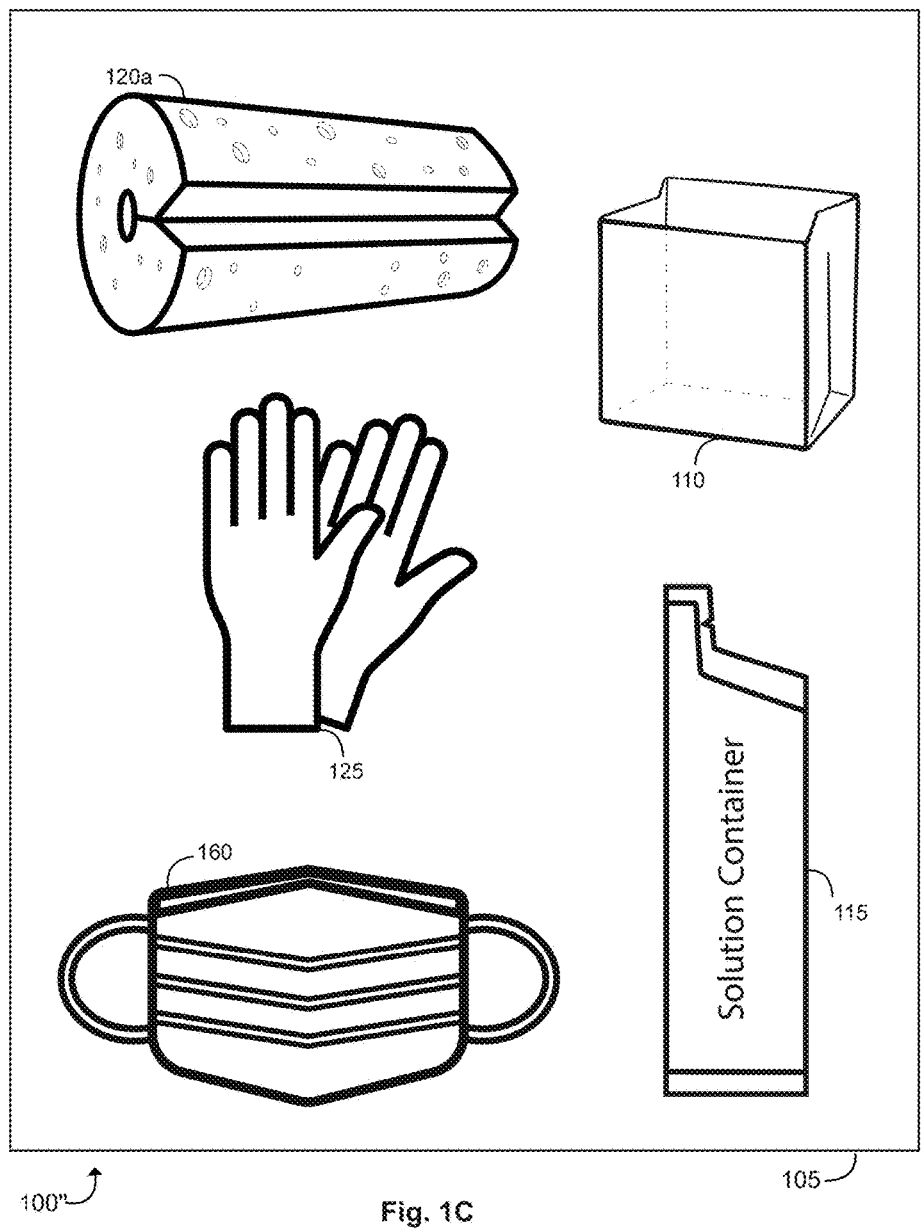
Figure 1D:
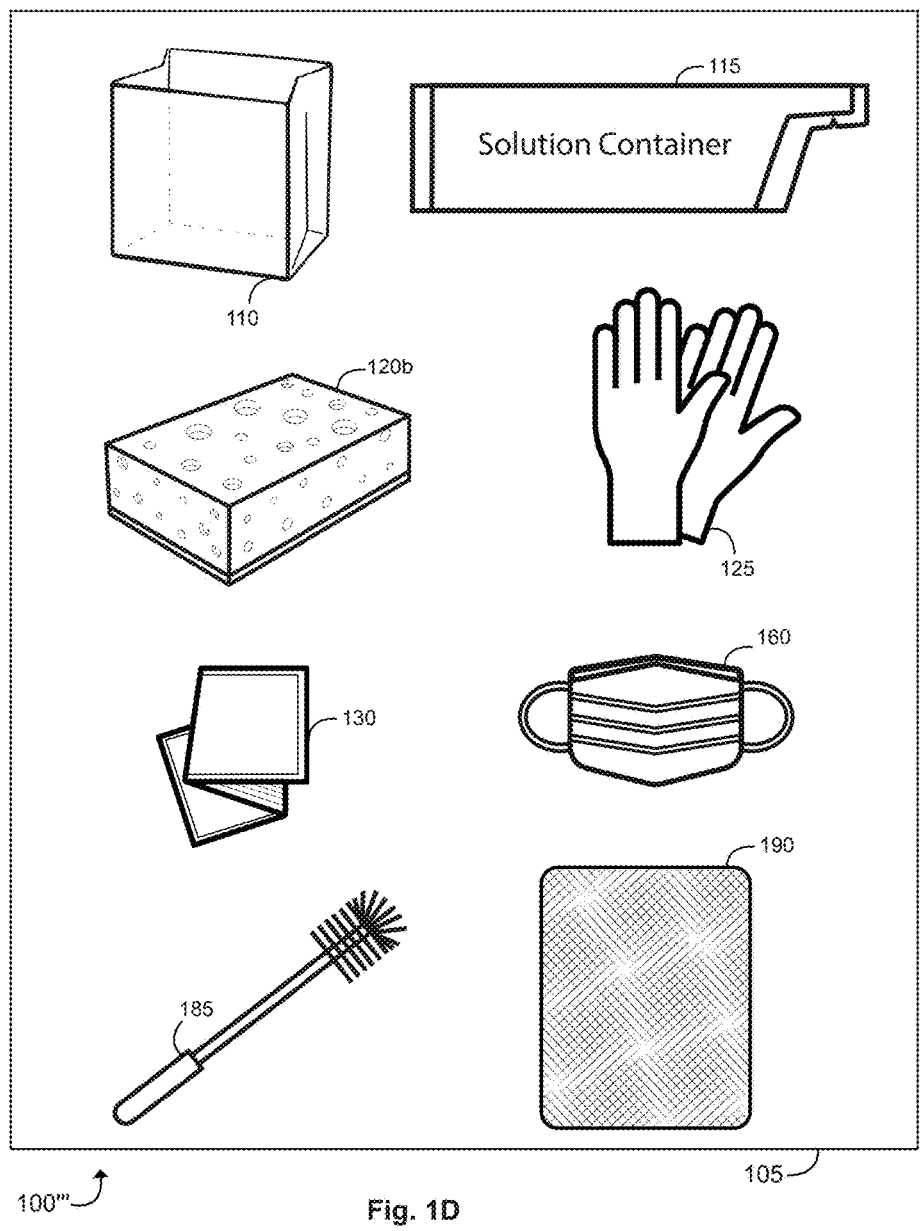

As shown in FIG. 1B, the medical kit 100 may include additional variations such as medical kit 100'. Medical kit 100' may further include additional components in addition to or separate from the inner bag 110, solution container 115, and/or absorbent pad 120. For example, the medical kit 100' may additionally include, without limitation, at least one of one or more pairs of gloves 125, a transport bag 130, lubricating jelly 135, one or more syringes 140, tubing 145, one or more sets of bite blocks 150, one or more suction tips 155, one or more face masks 160, one or more nasal cannulas 170, one or more electrodes 175, one or more tip guards 180, one or more brushes 185, gauze 190, one or more biohazard stickers 195, one or more bags containing water 197, or one or more valves (e.g., one or more air/water valves, one or more suction valves, one or more biopsy valves), and/or the like. The one or more pairs of gloves 125, transport bag 130, lubricating jelly 135, one or more syringes 140, tubing 145, one or more sets of bite blocks 150, one or more suction tips 155, one or more face masks 160, one or more nasal cannulas 170, one or more electrodes 175, one or more tip guards 180, one or more brushes 185, gauze 190, one or more biohazard stickers 195, one or more bags containing water 197, or one or more valves (e.g., one or more air/water valves, one or more suction valves, one or more biopsy valves), and/or the like, may be sterilized before or after being placed in medical kit 100'.

The transport bag 130 may be configured to transport medical instruments such as endoscopes after the medical instruments have been cleaned using components of medical kit 100'. The tubing 145 may be at least one of suction tubing, irrigation tubing, catheter, intravenous ("IV") drip tubing, or tourniquet, and/or the like. The one or more brushes 185 may include, but are not limited to, a standard endoscope brush, a double ended port and valve cleaning brush, a combination squeegee brush, or a channel cleaning brush, and/or the like.

Medical kit 100' may further include, without limitation, at least one of a plurality of pairs of gloves of different sizes, a plurality of transport bags of different sizes, a plurality of masks of different sizes, a plurality of nasal cannulas of different sizes, a plurality of tip guards of different sizes, or a plurality of brushes of different sizes, and/or the like.

The medical kit 100 may comprise any combination of these components listed above, plus any other component not listed above. There are almost an unlimited number of components that may be included in medical kit 100 and an almost unlimited number of ways to combine different components within medical kit 100. Additional variations of medical kit 100 (i.e., medical kit 100" and medical kit 100''') are shown in the non-limiting embodiments of FIGS. 1C and 1D. Medical kit 100" of FIG. 1C might include, without limitation, an inner bag 110, a solution container 115, a tubular sponge 120a, gloves 125, and medical mask 160, and/or the like. Medical kit 100''' of FIG. 1D might include, but is not limited to, an inner bag 110, a solution container 115, a square sponge 120b, one or more pairs of gloves 125, a transport bag 130, medical mask 160, brush 185, and gauze 190, and/or the like. However, medical kit 100 is not limited to only the embodiments displayed in the Figures.

By vacuum sealing the outer bag 105, components of the medical kit 100 such as inner bag 110, absorbent pad 120, gloves 125, transport bag 130, tubing 145, face masks 160, nasal cannulas 170, brushes 185, gauze 190, and/or the like may be compressed. Thus, medical kit 100 may take up less space and may be easier to store in hospitals, medical offices, dental offices, and/or the like. Further, by sterilizing the different components of medical kit 100 and vacuum sealing medical kit 100 in a sterile environment, the components of the medical kit 100 may be used in intensive care units, operating rooms, and/or the like.

FIGS. 2A-2E (collectively, "FIG. 2") are schematic diagrams illustrating a medical kit 200, in accordance with various embodiments.

Medical kit 200 may comprise a bag 205 (which may correspond to bag 105 of FIG. 1) and an absorbent pad 210 (collectively, "absorbent pad 210," which may correspond to absorbent pad 120 of FIG. 1). The bag 205 may be formed by at least two layer that are sealed together. Medical kit 200 may be formed by placing a solution (represented by droplet 230) on the absorbent pad 210 contained within the bag 205. The solution 230 (which may correspond to the solution contained within solution container 115 of FIG. 1) may be at least partially absorbed by the absorbent pad 210. The bag 205 may then be evacuated to create at least a partial vacuum seal surrounding the at least one absorbent pad 210 and the solution contained within the bag 205.

Figure 2A:
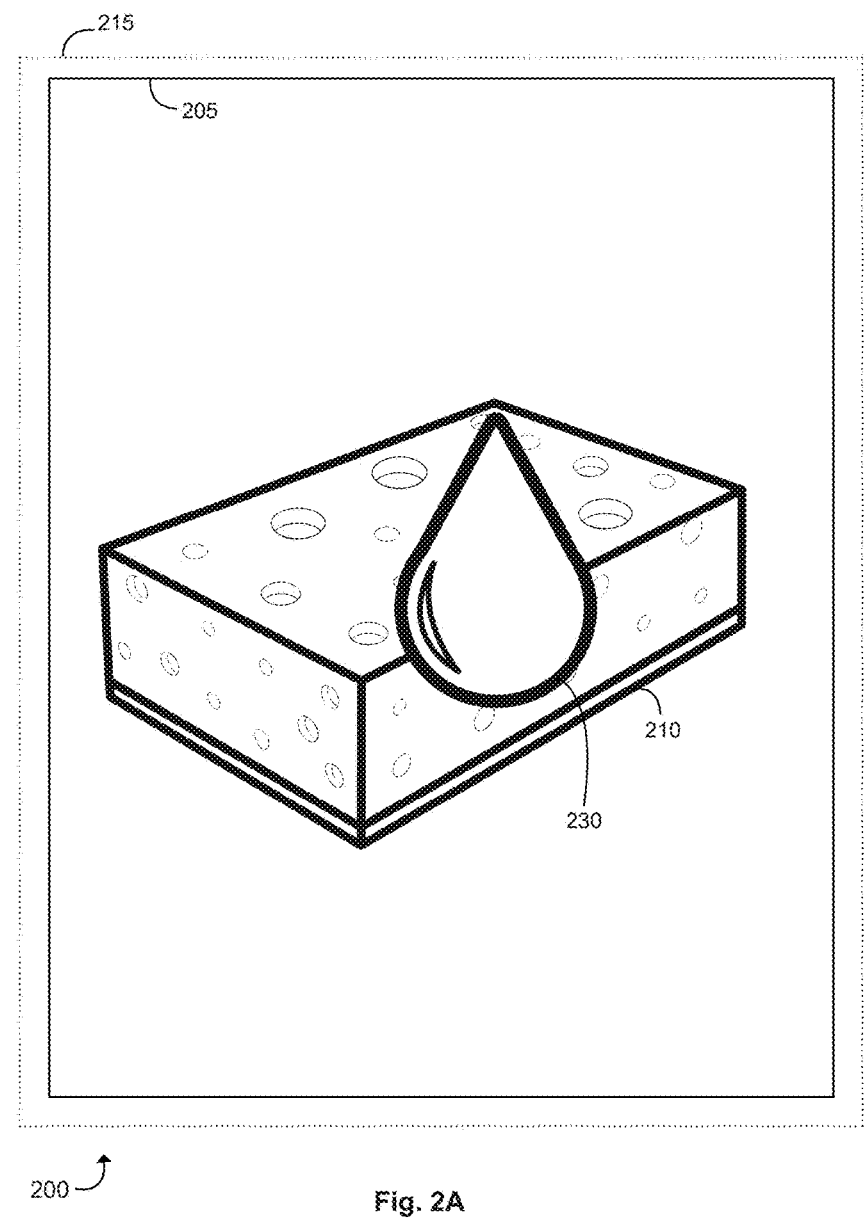
FIGS. 2A-2E are schematic diagrams illustrating another medical kit, in accordance with various embodiments.
Figure 2B:
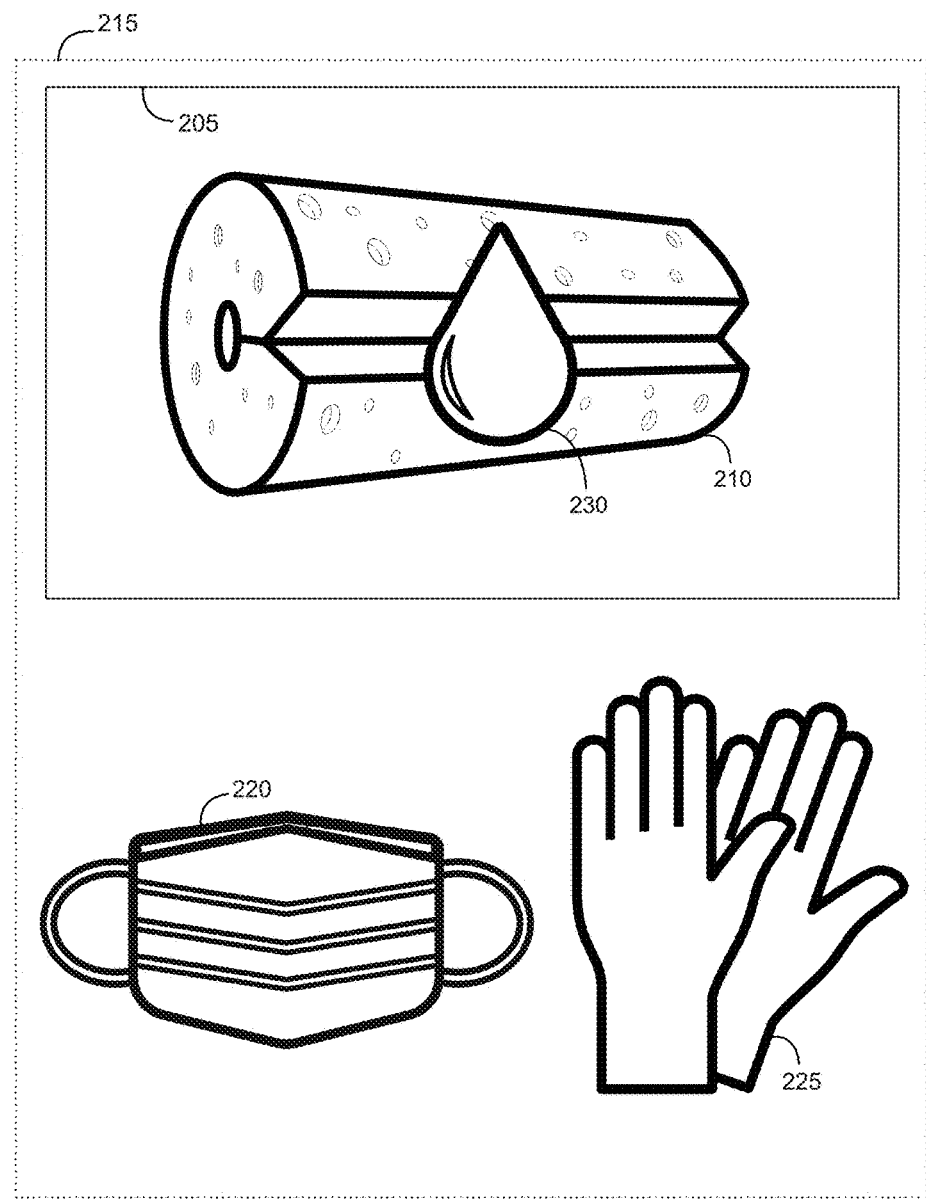
Figure 2C:
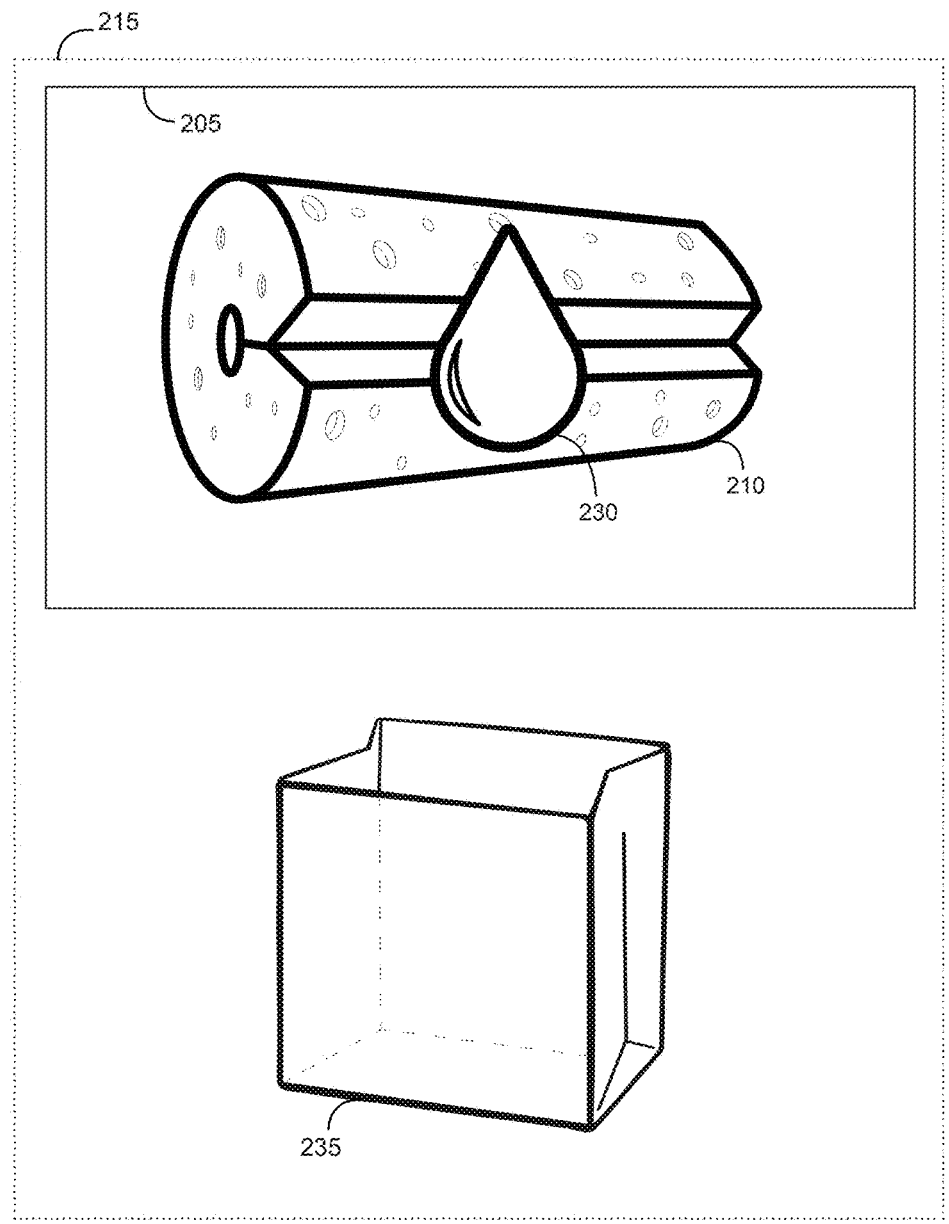
Figure 2D:
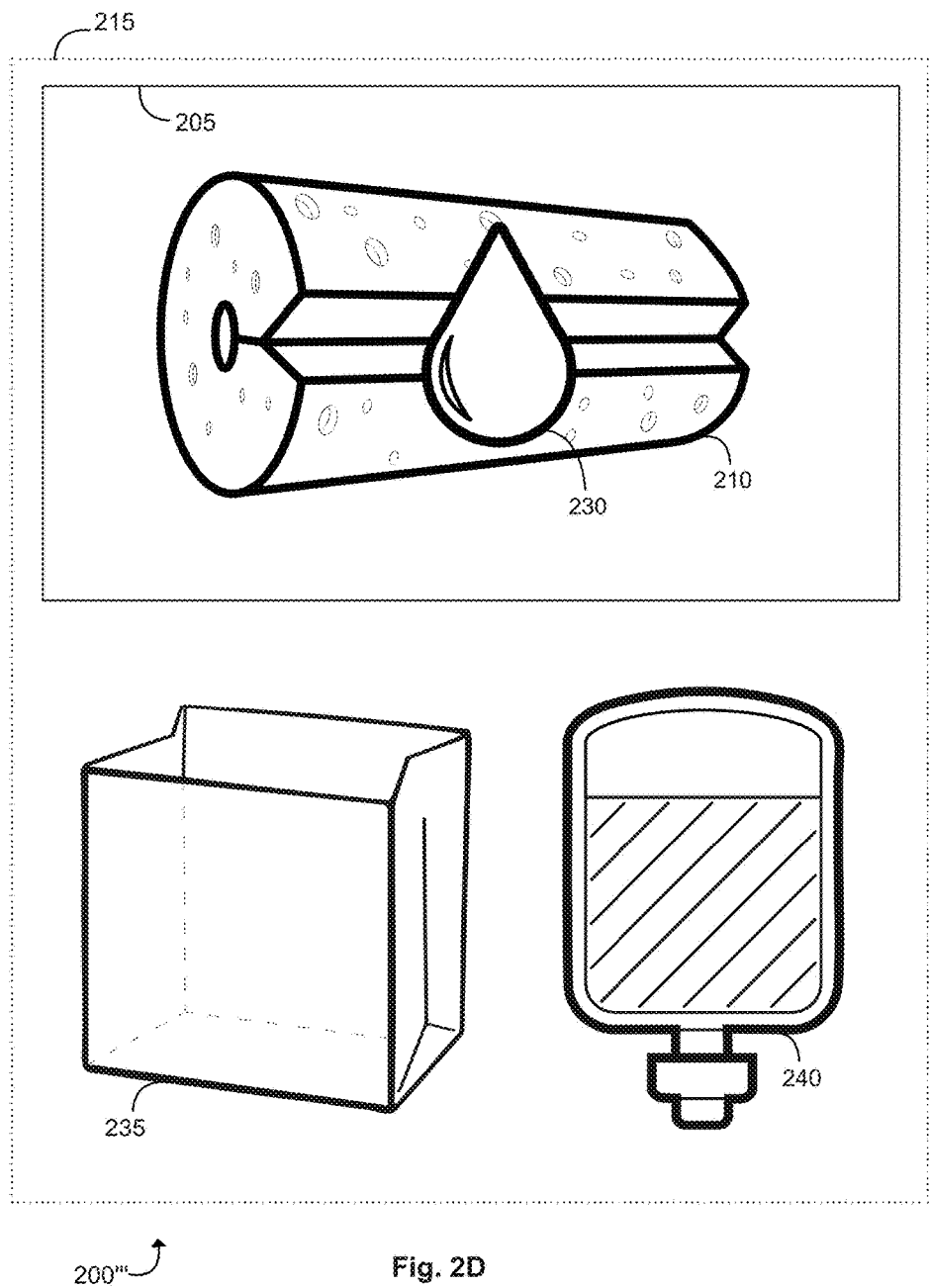
Figure 2E:
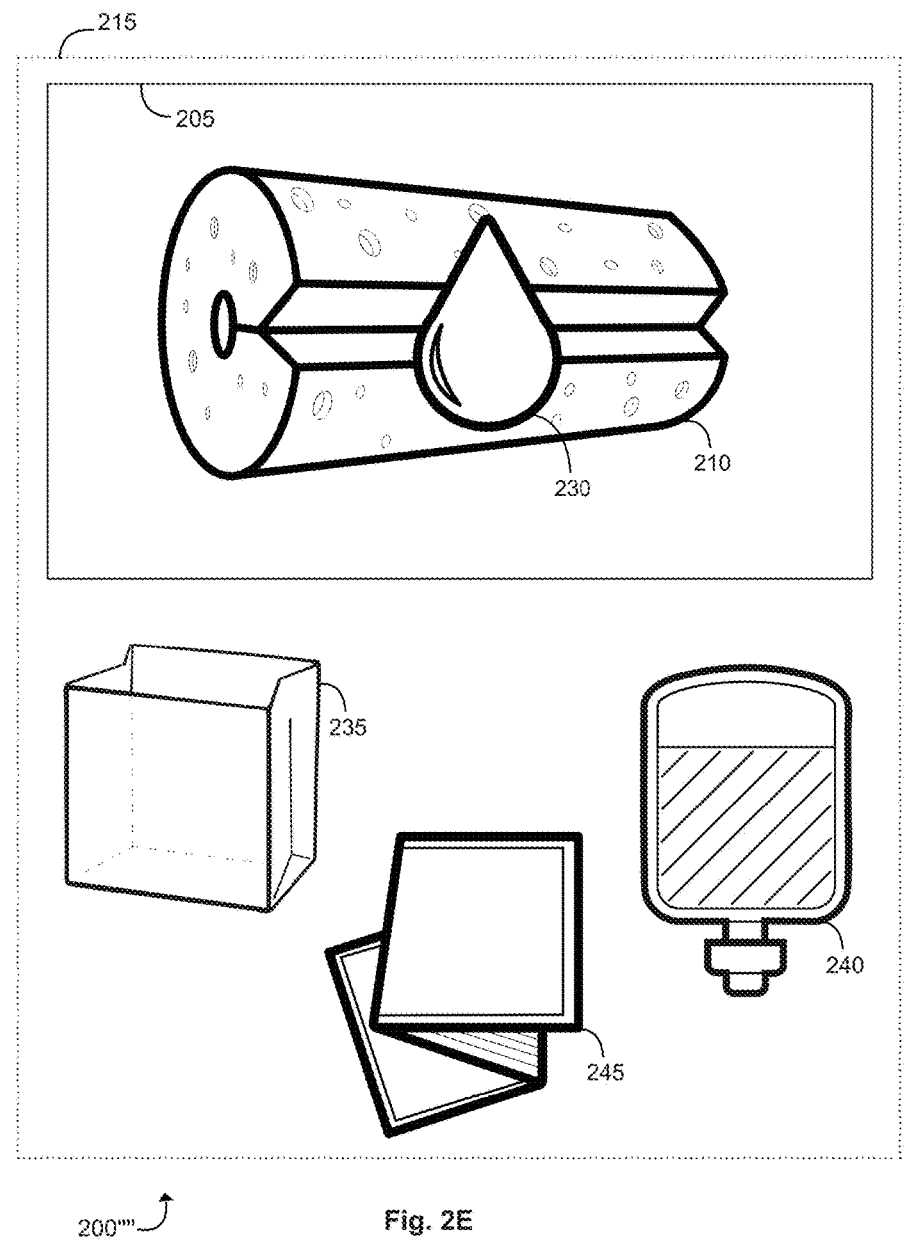

The vacuum sealed bag 205 may additionally be contained within a vacuum sealed outer bag 215. The vacuum sealed outer bag 215 may contain additional components of the medical kit 200 as shown by FIGS. 2B-2E (containing medical kit variations 200'-200'''). For example, as shown in FIG. 2B, the outer bag 215 may contain additional components such as one or more face masks 220 and one or more pairs of gloves 225. As shown in FIG. 2C, the outer bag 215 may contain additional components such as an inner bag 235 (which may correspond to inner bag 110 shown in FIG. 1). The outer bag 215 may additionally contain an inner bag 235 and one or more bags containing water 240, as shown in FIG. 2D. In various other embodiments, the outer bag 215 might contain, as shown FIG. 2E, an inner bag 235, one or more bags containing water 240, and one or more transport bags 245. FIGS. 2A-2E are supposed to be non-limiting examples of different medical kits 200 and each medical 200 might include any combination of an absorbent pad, one or more face masks, one or more gloves, one or more bags containing water, one or more inner bags, one or more transport bags, gauze, lubricating jelly, one or more syringes, tubing, one or more sets of bite blocks, one or more suction tips, one or more nasal cannulas, one or more electrodes, one or more tip guards, one or more brushes, gauze, one or more biohazard stickers, one or more valves (e.g., one or more air/water valves, one or more suction valves, one or more biopsy valves), and/or the like.

The vacuum sealed bag 205, absorbent pad 210, components of the medical kit 200 or 200', and the like, may be sterilized and maintained within a sterile environment within the vacuum sealed bag 205 and/or outer vacuum sealed bag 215.

Figure 3A:
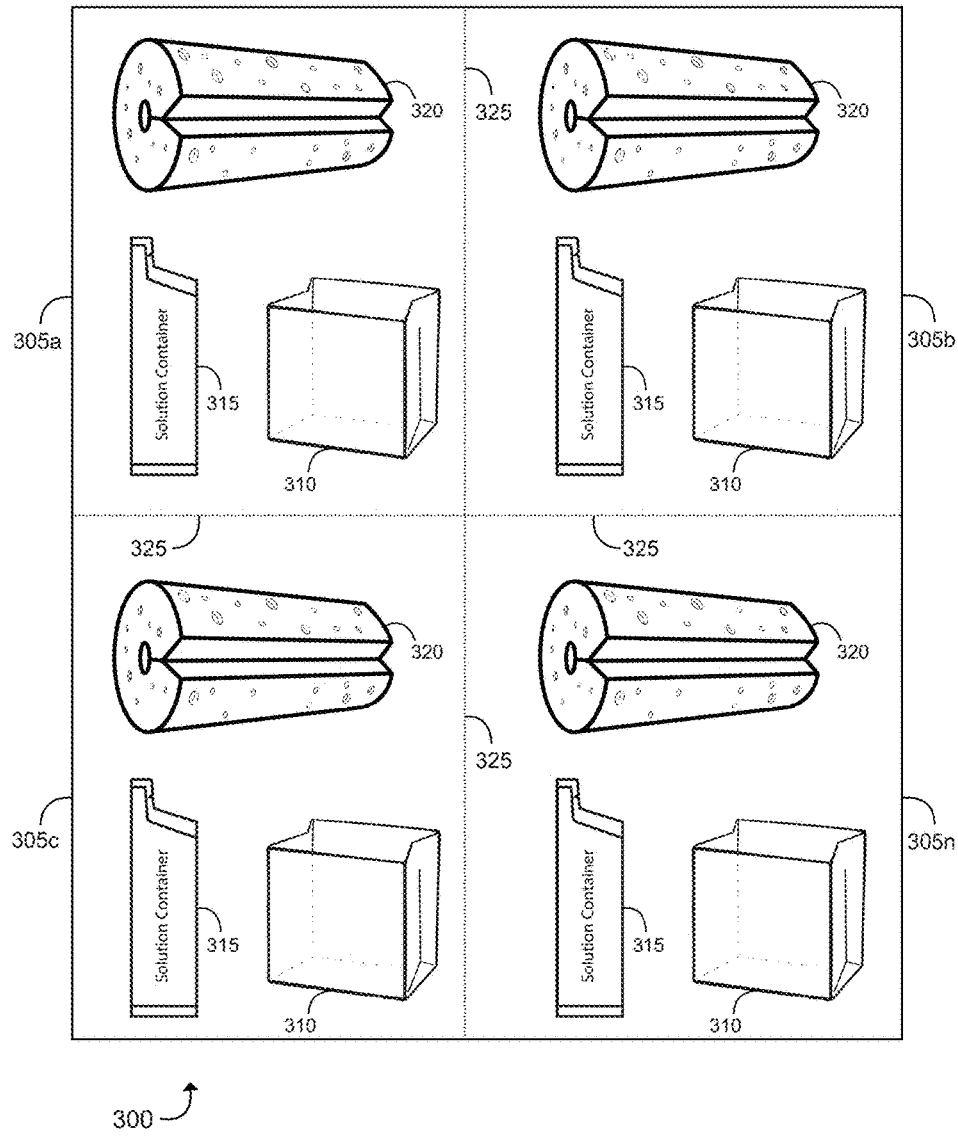
FIGS. 3A and 3B are schematic diagrams illustrating an embodiment comprising a set of a plurality of medical kits.
Figure 3B:
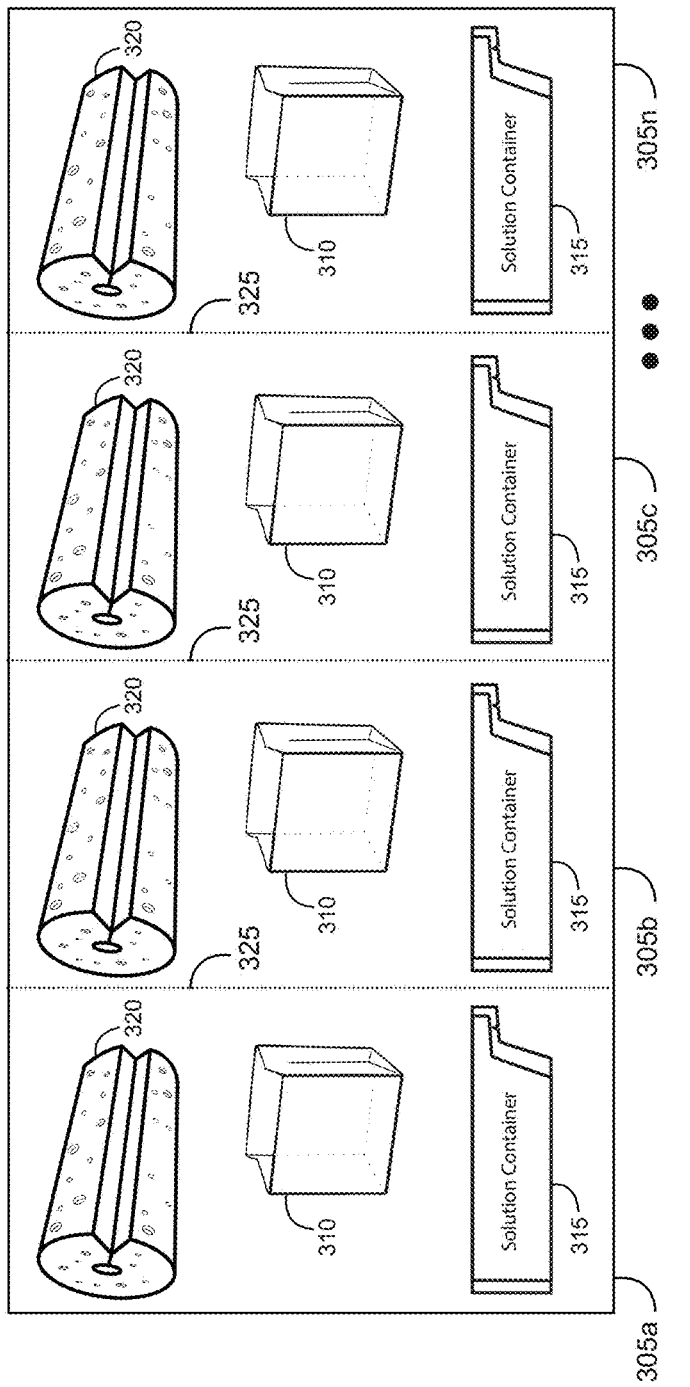

FIGS. 3A and 3B (collectively, "FIG. 3") are schematic diagrams illustrating various embodiments 300 or 300' of a set of a plurality of medical kits 305a-305n (collectively, "medical kits 305").

Medical kits 305 (which may correspond to medical kit 100 of FIG. 1 and/or medical kit 200 of FIG. 2) may be formed by providing a first layer of vacuum sealable material. The first layer of vacuum sealable material may be formed from at least one of a flexible or rigid film, a flexible or rigid plastic, or foam, and/or the like. The first layer may be formed to be a thin sheet of material or a tray, and/or the like. The first layer may further be formed from water and/or liquid-impermeable material to prevent leaks.

Next, components (e.g., an inner bag 310, a solution container 315, an absorbent pad 320, a partially vacuum sealed bag containing an absorbent pad in contact with solution, and/or other components) of the medical kit 305 may be placed on top of the first layer of vacuum sealable material. A second layer of vacuum sealable material may be placed over the components of medical kit 305. The second layer of vacuum sealable material may be formed from at least one of a flexible or rigid film, a flexible or rigid plastic, or foam, and/or the like. The second layer may further be formed from water and/or liquid-impermeable material to prevent leaks.

The first layer of vacuum sealable material and the second layer of vacuum sealable material may be held together via at least one of glue, tape, compression, thermosetting, adhesive-curing, or melting an end of the outer bag, and/or the like. The components of each medical kit 305 may then be vacuum sealed between the first layer of vacuum sealable material and the second layer of vacuum sealable material.

The components of the plurality of medical kits 305 may be vacuum sealed in a sterile environment and maintained in a sterile environment between the first layer of vacuum sealable material and the second layer of vacuum sealable material such that the contents of the medical kits 305 remain sterile and are available for immediate use (without the need for additional sterilization) in an operating room, intensive care unit, and/or the like.

One medical kit 305 and/or a plurality of medical kits 305 may be created using the method described above. If a plurality of medical kits 305 are created, then each medical kit 305 may be removably attached to another medical kit 305 via perforations 325. A doctor, dentist, medical practitioner, dental practitioner, and/or the like may easily detach one medical kit 305 from the others of the plurality of medical kits 305 via perforations 325.

The plurality of medical kits 305 may contain at least one of a plurality of pairs of gloves of different sizes, a plurality of transport bags of different sizes, a plurality of masks of different sizes, a plurality of nasal cannulas of different sizes, a plurality of tip guards of different sizes, or a plurality of brushes of different sizes, and/or the like. In a non-limiting example, a first medical kit of the plurality of medical kits 305 may contain small gloves, while a second medical kit of the plurality of medical kits may contain medium gloves, and so on. Thus, a user of the medical kit may order different medical kits to suit different purposes.

Additionally, and/or alternatively, each medical kit of the plurality of medical kits 305 may contain at least one of a plurality of pairs of gloves of different sizes, a plurality of transport bags of different sizes, a plurality of masks of different sizes, a plurality of nasal cannulas of different sizes, a plurality of tip guards of different sizes, or a plurality of brushes of different sizes, and/or the like.

By evacuating the air from the plurality of medical kits 305, the medical kits 305 are significantly smaller and take up less space than the medical kits currently sold in the medical and dental markets. Thus, a greater number of medical kits 305 may be stored in hospitals, medical offices, or dental offices, and/or the like.

Further, the standard medical kits sold in the medical and dental markets do not contain a sterile inner bag 310. Thus, medical kits (currently on the market) may first require sterilization before being used in an operating room, intensive care unit, and/or the like. By providing a sterile inner bag 310 within a first layer and a second layer, a medical practitioner can open medical kits 305 and use them immediately.

Figure 4A:
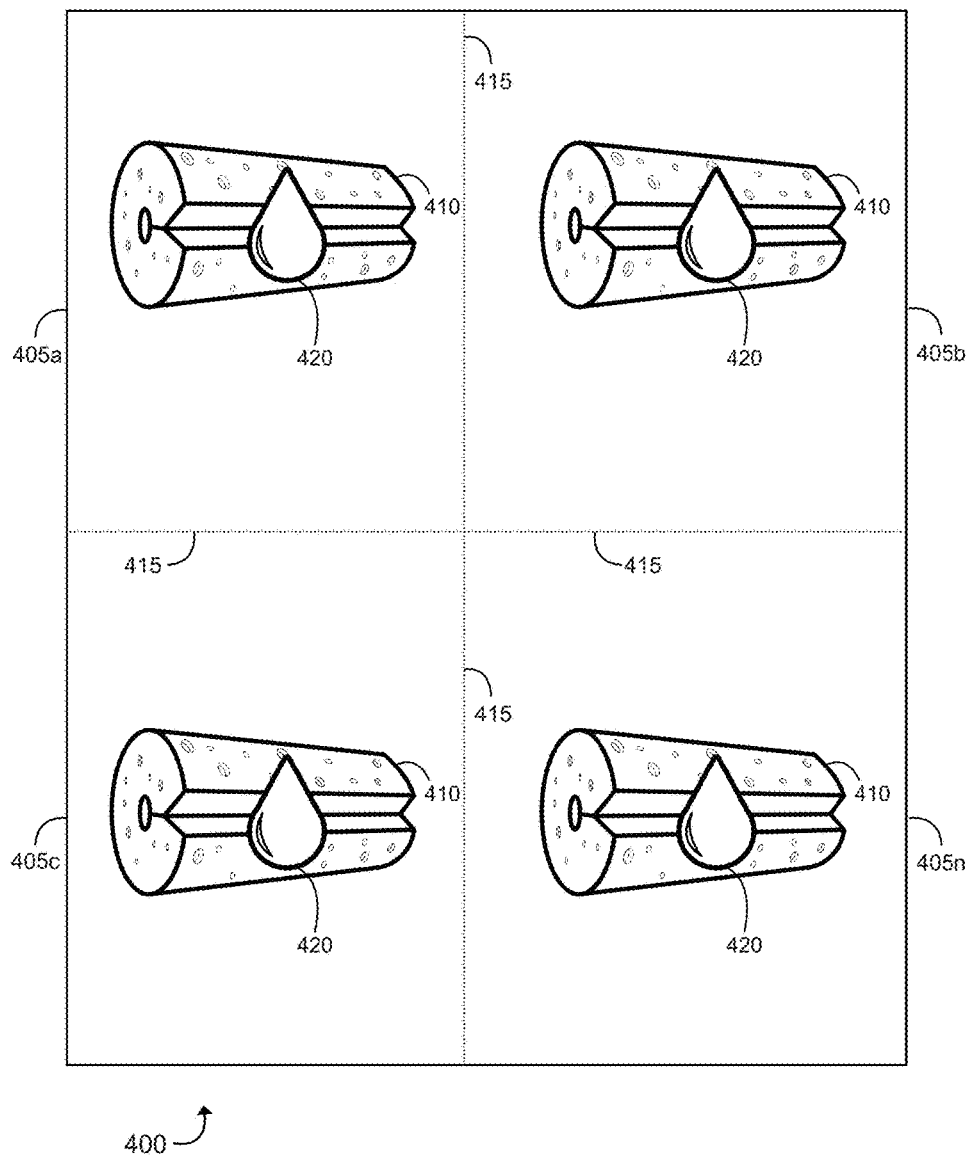
FIGS. 4A and 4B are schematic diagrams illustrating another embodiment comprising a set of a plurality of medical kits.
Figure 4B:
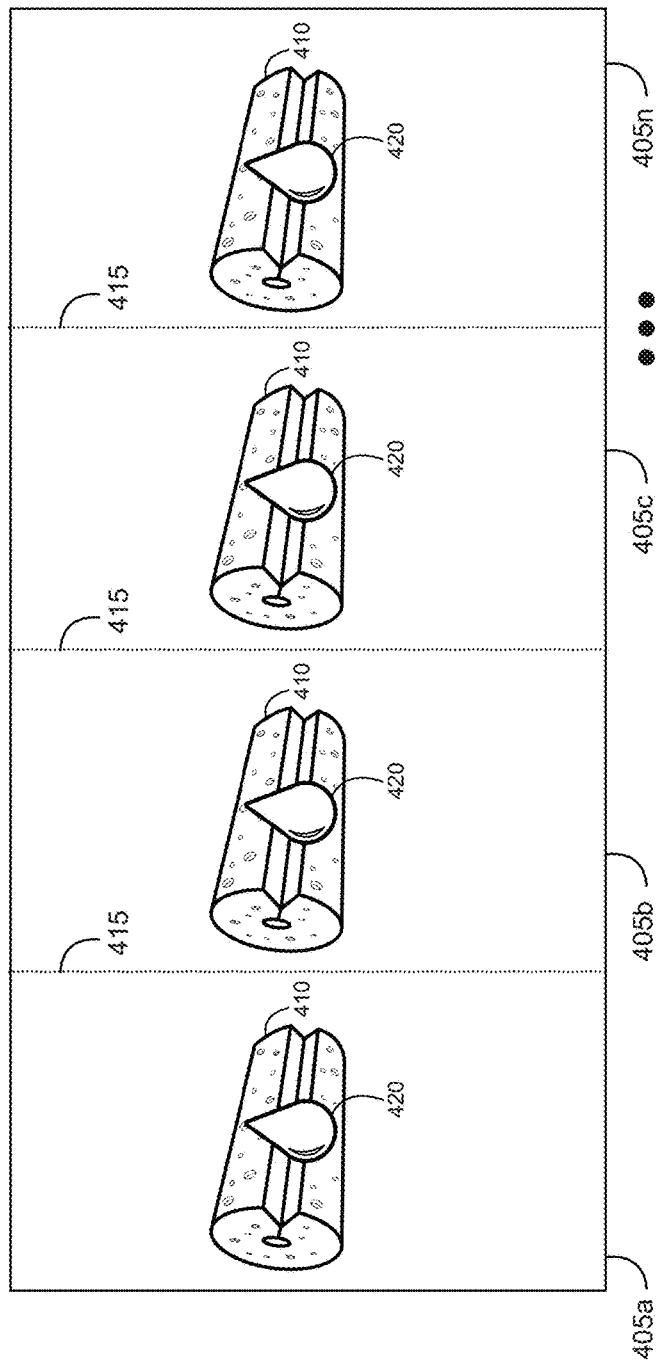

FIGS. 4A and 4B (collectively, "FIG. 4") are schematic diagrams illustrating various embodiments 400 or 400' of a set of a plurality of medical kits 405a-405n (collectively, "medical kits 405").

Medical kits 405 (which may correspond to medical kit 200 of FIG. 2) may be formed by providing a first layer of vacuum sealable material. The first layer of vacuum sealable material may be formed from at least one of a flexible or rigid film, a flexible or rigid plastic, or foam, and/or the like. The first layer may be formed to be a thin sheet of material, a tray, and/or the like. The first layer may further be formed from water and/or liquid-impermeable material to prevent leaks.

Next, components (e.g., an absorbent pad 410 in contact with solution (represented by droplet 420)) of the medical kit 405 may be placed on top of the first layer of vacuum sealable material. A second layer of vacuum sealable material may be placed over the components of medical kit 405. The second layer of vacuum sealable material may be formed from at least one of a flexible or rigid film, a flexible or rigid plastic, or foam, and/or the like. The second layer may further be formed from water and/or liquid-impermeable material to prevent leaks.

The first layer of vacuum sealable material and the second layer of vacuum sealable material may be held together via glue, tape, compression, thermosetting, adhesive-curing, or melting an end of the outer bag, and/or the like. The components of each medical kit 405 may then be at least partially vacuum sealed between the first layer of vacuum sealable material and the second layer of vacuum sealable material.

The components of the plurality of medical kits 405 may be vacuum sealed in a sterile environment and maintained in a sterile environment between the first layer of vacuum sealable material and the second layer of vacuum sealable material such that the contents of the medical kits 405 remain sterile and are available for immediate use (without the need for additional sterilization) in an operating room, intensive care unit, and/or the like.

One medical kit 405 and/or a plurality of medical kits 405 may be created using the method described above. If a plurality of medical kits 405 are created, then each medical kit 405 may be removably attached to another medical kit 405 via perforations 415. A doctor, dentist, medical practitioner, or dental practitioner, and/or the like, may easily detach one medical kit 405 from the plurality of medical kits 405 via perforations 415.

Each medical kit 405 may then be placed within an outer bag (not shown) and the outer bag may contain other components including at least one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, one or more biohazard stickers, one or more bags containing water, or one or more valves (e.g., one or more air/water valves, one or more suction valves, one or more biopsy valves), and/or the like. The outer bag may be vacuum sealed around medical kits 405, similar to the process described above and similar to the process described with respect to FIG. 3.

By evacuating the air from the plurality of medical kits 405 and/or an outer bag surrounding medical kits 405, the medical kits 405 are significantly smaller and take up less space than the medical kits currently sold in the medical and dental markets. Thus, a greater number of medical kits 405 may be stored in hospitals, medical offices, or dental offices, and/or the like.

Figure 5A:
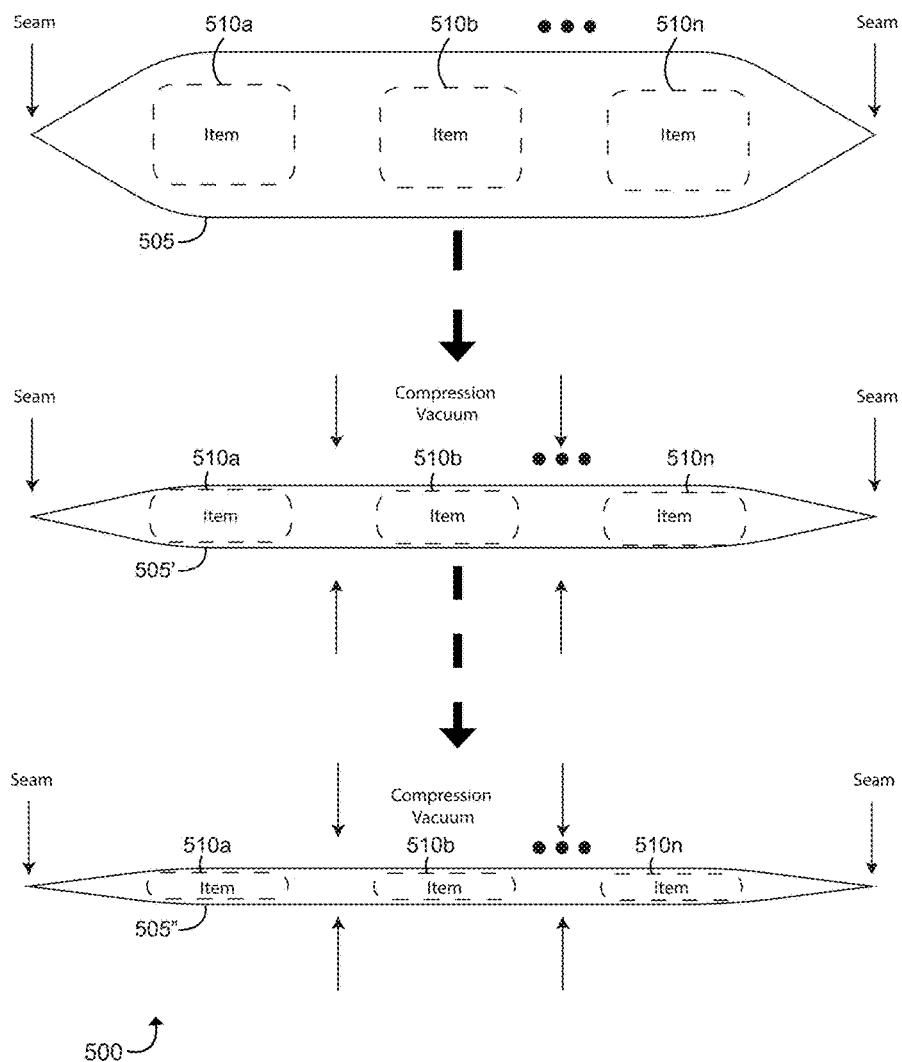

Turning to FIGS. 5A and 5B (collectively, "FIG. 5"), FIGS. 5A and 5B are schematic diagrams illustrating a vacuum sealing process 500 or 500' for vacuum sealing one or more medical kits 505 (which may correspond to medical kits 100 (or 100', 100", or 100'''), 200 (or 200', 200", 200''', or 200''''), 305a-305n, and 405a-405n of FIGS. 1, 2, 3, and 4, respectively), in accordance with various embodiments.

As shown in FIG. 5A, medical kit 505 represents a medical kit before it has been vacuum sealed. Medical kit 505' represents a medical kit while it is being vacuum sealed. Medical kit 505" represents a medical kit after it has been vacuum sealed. The medical kit(s) 505, 505', and 505" may have one or more items 510a-510n (collectively, "items 510"). The one or more items 510 may include, without limitation, at least one of one or more inner bags, one or more absorbent pads, one or more solution containers, one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, one or more biohazard stickers, one or more bags containing water, or one or more valves (e.g., one or more air/water valves, one or more suction valves, one or more biopsy valves), and/or the like.

As shown in FIG. 5B, medical kit 515 represents a medical kit before it has been vacuum sealed. Medical kit 515' represents a medical kit while it is being vacuum sealed. Medical kit 515" represents a medical kit after it has been at least partially vacuum sealed. An at least partially vacuum sealed medical kit might have most, but not all of the air evacuated from it. The medical kit(s) 515, 515', and 515" may have one or more absorbent pads 520 in contact with a solution (represented by droplet 525).

As shown in FIGS. 5A and 5B, by evacuating the air from the one or more medical kits 505 and 515, the medical kits 505" and 515" (after being at least partially vacuum sealed) are significantly smaller and take up less space than the medical kits currently sold in the medical and dental markets. Thus, a greater number of medical kits 505" and 515" may be stored in hospitals, medical offices, or dental offices, and/or the like.

Turning to FIGS. 6A-6E (collectively, "FIG. 6"), FIGS. 6A-6E are schematic diagrams illustrating a plurality of systems 600a-600e for storing a plurality of medical kits 605a-605n (collectively, "medical kits 605"), in accordance with various embodiments.

There are a variety of ways that medical kits 605 (which may correspond to medical kit 100 (or 100', 100", or 100''') of FIG. 1, medical kit 200 (or 200') of FIG. 2, medical kits 305a-305n of FIG. 3, medical kits 405a-405n of FIG. 4, and medical kits 505 and 515 of FIG. 5, and/or the like) may be stored.

Figure 6A:
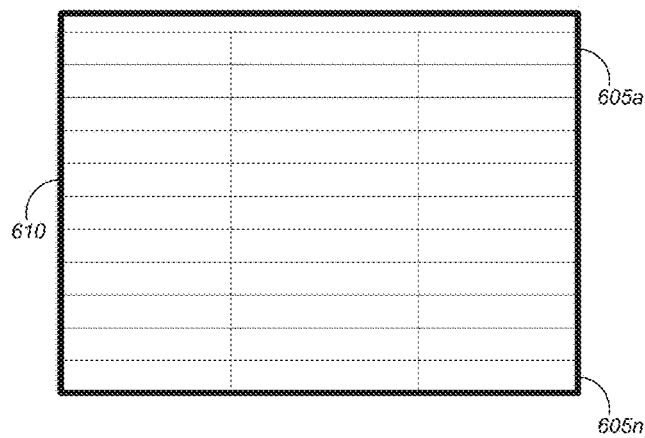
FIGS. 6A-6E are schematic diagrams illustrating a plurality of systems for storing/dispensing a plurality of medical kits, in accordance with various embodiments.

For example, as shown in FIG. 6A, system 600a might comprise a box 610. A predetermined number of medical kits 605 may be stored in box 610. Storing medical kits 605 in box 610 would be simple because medical kits 605 may simply be stored in the box in which they are shipped. The box 610 may contain more medical kits 605 than standard medical kits that are currently in use because the air has been evacuated from medical kits 605.

Figure 6B:
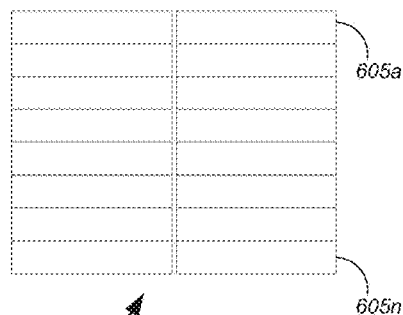

Additionally, and/or alternatively, as shown in FIG. 6B, medical kits 605 may be stored by stacking a plurality of medical kits 605 on top of each other.

Figure 6C:
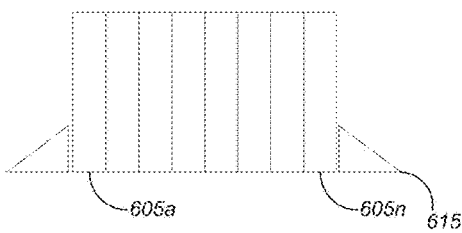

In an additional embodiment, shown by system 600c of FIG. 6C, medical kits 605 may be stored by aligning a predetermined number of medical kits 605 on an edge of each medical kit 605. The predetermined number of medical kits 605 may then be held together by bookends 615, or the like, to ensure the medical kits 605 do not fall.

Figure 6D:
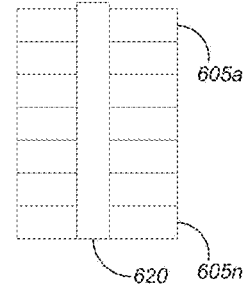

In another embodiment, shown in FIG. 6D, a predetermined amount of medical kits 605 may be removably attached together. Medical kits 605 may be removably attached together via attachment 620. Removable attachment 620 may be at least one of a plastic strap, an elastic strap, an elastic cord, and/or the like.

Figure 6E:
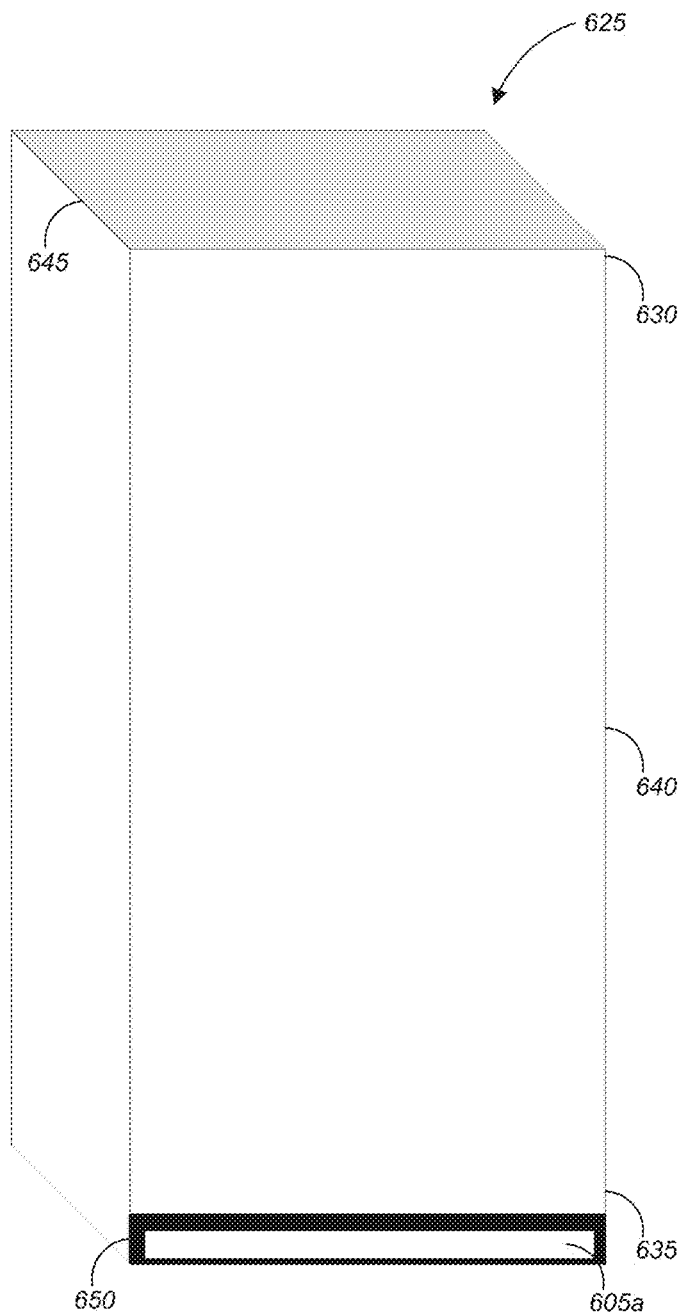

In yet another embodiment, shown in FIG. 6E, a plurality of medical kits 605 may be stored in container 625. The container 625 may comprise a top 630, a bottom 635, and a body 640 between the top 630 and the bottom 635.

A plurality of medical kits 605 may be disposed within the body 640 of the container 625. Each medical kit 605 may comprise one outer bag containing one or more of at least one inner bag, at least one solution container, or at least one absorbent pad, and/or the like. The outer bag may be evacuated to form a vacuum seal surrounding the one or more of the at least one inner bag, the at least one solution container, or the at least one absorbent pad, and/or the like.

The container 625 may further comprise (although it is not required) a lid 645 attached to the top 630 of the container 625. A user may open the lid 645 of the container 625 to insert additional medical kits 605 into the container 625.

An opening 650 may be disposed near the bottom 635 of the container 625. The opening 650 may be configured to dispense at least one medical kit 605 at a time from the bottom 635 of the container 625. The medical kits 605 may be dispensed using gravity. For example, as at least one medical kit 605 is pulled from the opening 650, gravity may cause another medical kit 605 to drop to the bottom 635 of the container 625.

The medical kit 605 may protrude from the opening 650 of the container 625. Additionally, and/or alternatively, pulling/removing one medical kit from the container 625 may cause an additional medical kit 605 to protrude slightly from the opening 650 of the container 625.

The plurality of medical kits 605 within the container 625 may be attached together via perforations. In order to remove a medical kit attached to a plurality of medical kits via perforations, the container 625 may further comprise (at the bottom 635 of the container 625) at least four spring loaded tabs and a hand tab on either side of the body 640 near the bottom 635. The plurality of medical kits 605 when disposed in the body 640 are arranged such that the perforations are adjacent to the sides of the body 640.

Removing one of the at least one medical kit 605 by pulling a non-perforated side of the medical kit 605 via one of the hand tabs causes the spring-loaded tabs to flex and rebound to prevent the next medical kit 605 from falling. The resultant hanging medical kit can then be removed by tearing along the perforations. The bottom 635 of the container 625 may be configured to aid a user to tear along the perforations of the one or more medical kits 605.

FIG. 6 represents a few of the possible ways a plurality of medical kits 605 may be stored. Because the air has been evacuated from medical kits 605, hospitals, medical offices, or dental offices, and/or the like, can store more medical kits 605 and medical kits 605 can take up less space in hospitals, medical offices, or dental offices, and/or the like. Further, because the components of medical kits 605 may be sterilized and maintained within a sterile environment, medical kits 605 may be used immediately in intensive care units, operating rooms, and/or the like.

Figure 7:
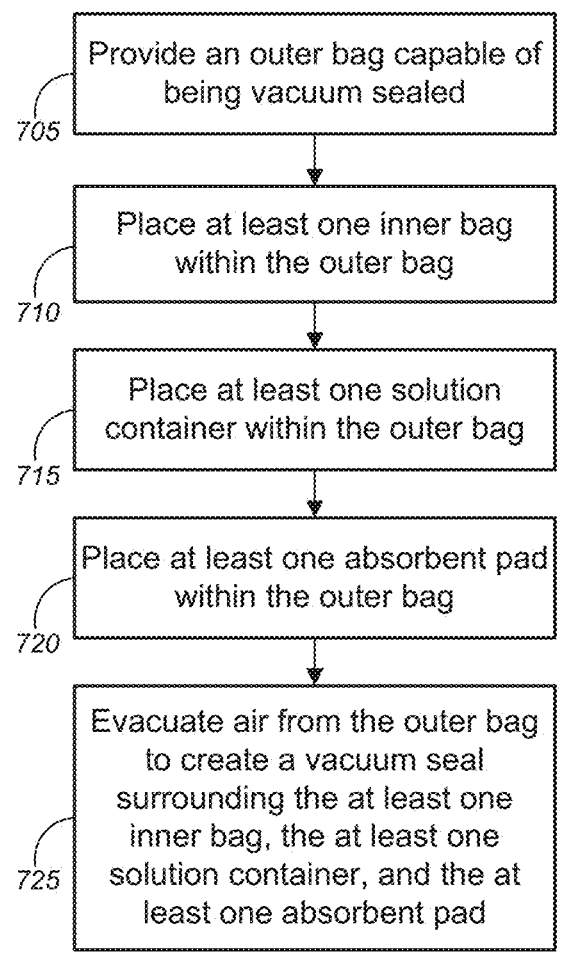
FIG. 7 is a flow diagram illustrating a method for vacuum packing medical kits, in accordance with various embodiments.

FIG. 7 is a flow diagram illustrating a method 700 for implementing a method for vacuum packing medical kits, in accordance with various embodiments. While the techniques and procedures are depicted and/or described in a certain order for purposes of illustration, it should be appreciated that certain procedures may be reordered and/or omitted within the scope of various embodiments. Moreover, while the method 700 illustrated by FIG. 7 can be implemented by or with (and, in some cases, are described below with respect to) the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, 4, 5, and 6 respectively (or components thereof), such methods may also be implemented using any suitable implementation. Similarly, while each of the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, 4, 5, and 6 respectively (or components thereof), can operate according to the method 700 illustrated by FIG. 7, the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, 4, 5, and 6 can each also operate according to other modes of operation.

In the non-limiting embodiment of FIG. 7, method 700, at block 705, may comprise providing an outer bag capable of being vacuum sealed. The outer bag capable of being vacuum sealed may be made from a vacuum sealable material and/or liquid-impermeable material such as film, plastic, and/or the like. At block 710, the method 700 may further comprise placing at least one inner bag within the outer bag. A solution container may then be placed within the bag (block 715). Next, at least one absorbent pad may be placed within the outer bag (block 720).

Next, the method 700, at block 725, may further comprise evacuating air from the outer bag to create a vacuum seal surrounding the at least one inner bag, the at least one solution container, and the at least one absorbent pad. By evacuating the bag containing the at least one inner bag, the at least one solution container, and the at least one absorbent pad, the size of the bag may be reduced.

The outer bag may then be sealed with at least one of glue, tape, compression, thermosetting, adhesive-curing, or melting an end of the outer bag, and/or the like.

Additionally, and/or alternatively, the outer bag may comprise one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, biohazard stickers, one or more bags containing water, or one or more valves (e.g., one or more air/water valves, one or more suction valves, one or more biopsy valves), and/or the like.

Further, the components contained within the outer bag may be sterilized such that the components are available for immediate use when the outer bag is opened.

Figure 8:
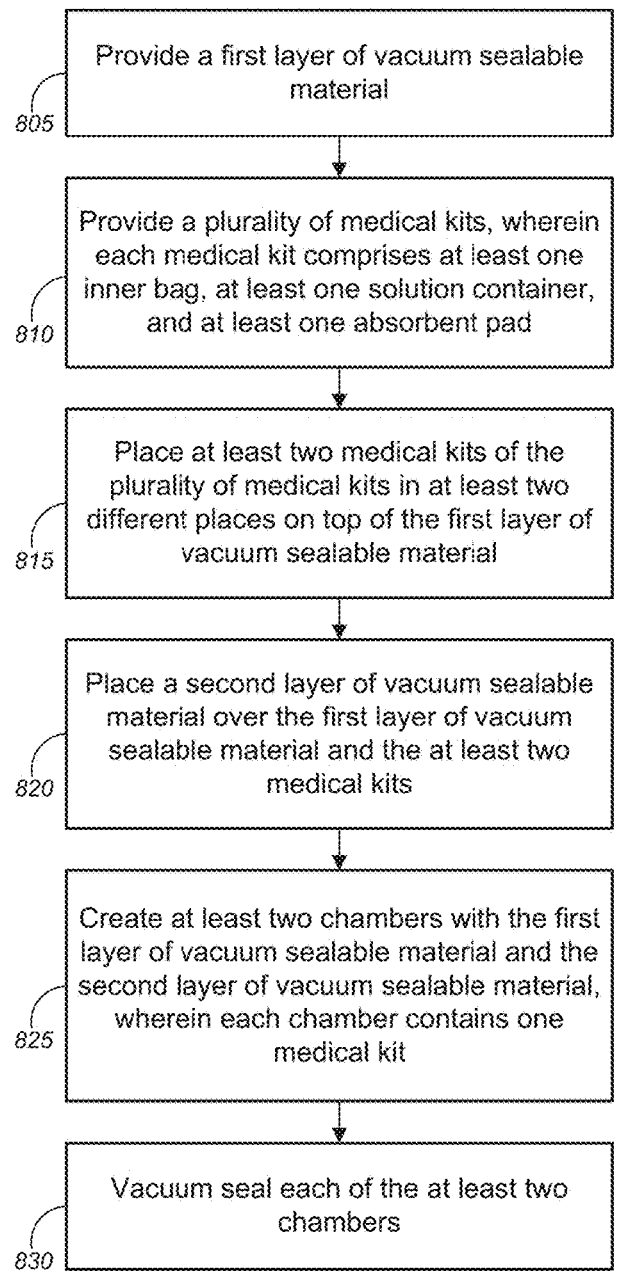
FIG. 8 is a flow diagram illustrating a method for vacuum packing a plurality of medical kits, in accordance with various embodiments.

FIG. 8 is a flow diagram illustrating a method 800 for implementing a method for vacuum packing a plurality of medical kits, in accordance with various embodiments.

While the techniques and procedures are depicted and/or described in a certain order for purposes of illustration, it should be appreciated that certain procedures may be reordered and/or omitted within the scope of various embodiments. Moreover, while the method 800 illustrated by FIG. 8 can be implemented by or with (and, in some cases, are described below with respect to) the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, 4, 5, and 6 respectively (or components thereof), such methods may also be implemented using any suitable implementation. Similarly, while each of the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, 4, 5, and 6 respectively (or components thereof), can operate according to the method 800 illustrated by FIG. 8, the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, and 4, 5, and 6 can each also operate according to other modes of operation.

In the non-limiting embodiment of FIG. 8, method 800, at block 805, may comprise providing a first layer of vacuum sealable material. The first layer of vacuum sealable material may be formed from at least one of a flexible or rigid film, a flexible or rigid plastic, foam, or other material that is vacuum sealable. The first layer may be formed to be a thin sheet of material, a tray, and/or the like. Additionally, and/or alternatively, the first layer of vacuum sealable material may be made from liquid-impermeable material such as a film, a plastic, or other material that is liquid-impermeable.

At block 810, the method 800 may further comprise providing a plurality of medical kits. Each medical kit might have at least one inner bag, at least one solution container, and/or at least one absorbent pad.

Each medical kit may further include, without limitation, one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, biohazard stickers, one or more bags containing water, or one or more valves (e.g., one or more air/water valves, one or more suction valves, one or more biopsy valves), and/or the like. Additionally, and/or alternatively, each medical kit may include, but is not limited to, at least one of a plurality of pairs of gloves of different sizes, a plurality of transport bags of different sizes, a plurality of masks of different sizes, a plurality of nasal cannulas of different sizes, a plurality of tip guards of different sizes, or a plurality of brushes of different sizes, and/or the like.

Method 800, at block 815, may also comprise placing at least two medical kits of the plurality of medical kits in at least two different places on top of the first layer of vacuum sealable material. A predetermined amount of medical kits may be placed on the first layer of vacuum sealable material. Additionally, and/or alternatively, method 800, at block 820, may comprise placing a second layer of vacuum sealable material over the first layer of vacuum sealable material and the at least two medical kits. The second layer of vacuum sealable material may be formed from at least one of a flexible or rigid film, a flexible or rigid plastic, foam, or other material that is capable of being vacuum sealed. Additionally, and/or alternatively, the second layer of vacuum sealable material may be made from liquid-impermeable material such as a film, a plastic, or other material that is liquid-impermeable.

Each medical kit may contain different components. In a non-limiting example, a first medical kit may contain small gloves while a second medical kit may contain large gloves, and so on. In this manner, each medical kit may be tailored to serve a particular purpose and/or to be used by a particular user(s).

Each component of the medical kit (e.g., at least one inner bag, at least one solution container, at least one absorbent pad, and/or the like) may be sterilized before being placed on the first layer. Additionally, and/or alternatively, the first layer of the medical kit and the second layer of the medical kit may be sterilized.

Next, method 800, at block 825, may comprise creating at least two chambers with the first layer of vacuum sealable material and the second layer of vacuum sealable material, wherein each chamber contains one medical kit. The first layer and second layer may surround the medical kit creating the chamber containing one medical kit. The at least two chambers (each containing one medical kit) may be removably attached to each other. The at least two chambers may be attached to one another via one or more perforations between each chamber. The at least two chambers may be detachable from one another via the one or more perforations between each chamber. Additionally, and/or alternatively, the at least two chambers may be configured to be attached to one another via at least one of a string, a strip of plastic, or tape, and/or the like.

The at least two chambers may be configured to be stacked on top of each other (for storage). Additionally, and/or alternatively, the at least two chambers may be configured to stand upright on edges corresponding to the at least two chambers. The at least two chambers may be stored by stacking the at least two chambers on top of one another and/or attaching a specified number of chambers together and placing the specified number of chambers upright on edges corresponding to the specified number of chambers.

At block 830, method 800 may additionally comprise vacuum sealing each of the at least two chambers (and/or evacuating air from the at least two chambers). By evacuating air from the at least two chambers, components of the medical kit such as the absorbent pad may be compressed thereby reducing the size of the medical kits. Further, the chambers may be evacuated in a sterile environment to maintain a sterile environment for containing one or more components of the medical kit. When the chambers are opened, components of the medical kit may be immediately used in intensive care units, operating rooms, and/or the like.

Figure 9:
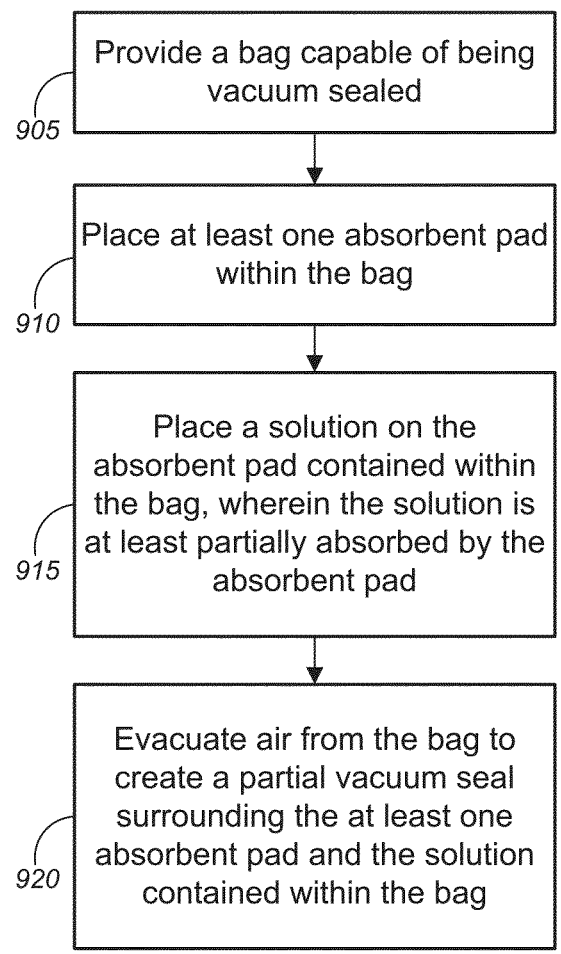
FIG. 9 is a flow diagram illustrating a method for vacuum packing medical kits, in accordance with various embodiments.

FIG. 9 is a flow diagram illustrating a method 900 for implementing a method for vacuum packing a plurality of medical kits, in accordance with various embodiments.

While the techniques and procedures are depicted and/or described in a certain order for purposes of illustration, it should be appreciated that certain procedures may be reordered and/or omitted within the scope of various embodiments. Moreover, while the method 900 illustrated by FIG. 9 can be implemented by or with (and, in some cases, are described below with respect to) the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, 4, 5, and 6 respectively (or components thereof), such methods may also be implemented using any suitable implementation. Similarly, while each of the medical kits, sets, processes, or systems 100 (or 100', 100", or 100'''), 200 (or 200'), 300 (or 300'), 400 (or 400'), 500 (or 500'), and 600a-600e respectively (or components thereof), can operate according to the method 900 illustrated by FIG. 9, the medical kits, sets, processes, or systems 100 (or 100', 100", or 100'''), 200 (or 200'), 300 (or 300'), 400 (or 400'), 500 (or 500'), and 600a-600e can each also operate according to other modes of operation.

In the non-limiting embodiment of FIG. 9, method 900, at block 905, may comprise providing a bag capable of being vacuum sealed. The bag capable of being vacuum sealed may be made from a vacuum sealable material and/or liquid-impermeable material such as film, plastic, and/or the like. At block 910, the method 900 may further comprise placing at least one absorbent pad within the bag. A solution may then be placed on the absorbent pad contained within the bag, and the solution may be at least partially absorbed by the absorbent pad (block 915).

Next, the method 900, at block 920, may further comprise evacuating air from the bag to create a partial vacuum seal surrounding the at least one absorbent pad and the solution contained within the bag. By evacuating the bag containing the absorbent pad and the solution, the size of the bag may be reduced.

The bag containing the absorbent pad and the solution may then be sealed with at least one of glue, tape, compression, thermosetting, adhesive-curing, or melting an end of the outer bag, and/or the like.

Additionally, and/or alternatively, the partially evacuated bag containing the absorbent pad and the solution may be placed in an outer bag comprising other components of a medical kit. The other components of the medical kit may comprise one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, biohazard stickers, one or more bags containing water, or one or more valves (e.g., one or more air/water valves, one or more suction valves, one or more biopsy valves), and/or the like.

The outer bag comprising the bag containing the absorbent pad and the solution and other components of the medical kit may then be vacuum sealed. By evacuating the outer bag, the size of the outer bag may be reduced. Further, the components contained within the outer bag may be sterilized such that the components are available for immediate use when the outer bag is opened.

Figure 10:
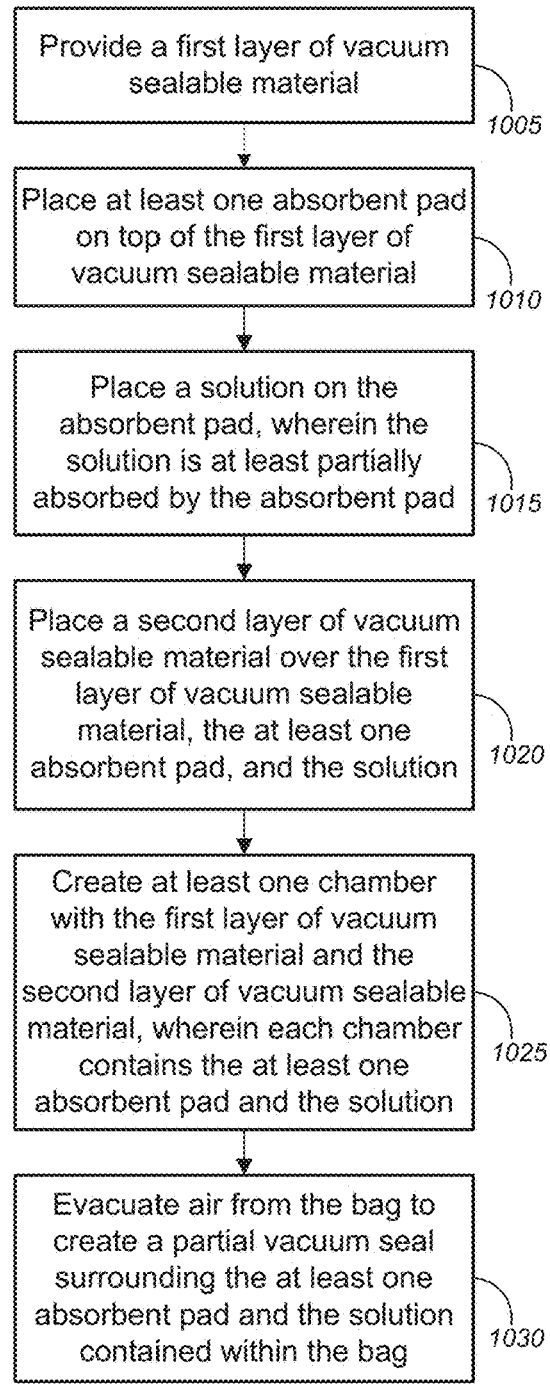
FIG. 10 is a flow diagram illustrating a method for vacuum packing a plurality of medical kits, in accordance with various embodiments.

FIG. 10 is a flow diagram illustrating a method 1000 for implementing a method for vacuum packing a plurality of medical kits, in accordance with various embodiments.

While the techniques and procedures are depicted and/or described in a certain order for purposes of illustration, it should be appreciated that certain procedures may be reordered and/or omitted within the scope of various embodiments. Moreover, while the method 1000 illustrated by FIG. 10 can be implemented by or with (and, in some cases, are described below with respect to) the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, 4, 5, and 6 respectively (or components thereof), such methods may also be implemented using any suitable implementation. Similarly, while each of the medical kits, sets, processes, or systems 100 (or 100', 100", or 100'''), 200 (or 200'), 300 (or 300'), 400 (or 400'), 500 (or 500'), and 600a-600e of FIGS. 1, 2, 3, 4, 5, and 6 respectively (or components thereof), can operate according to the method 1000 illustrated by FIG. 10, the medical kits, sets, processes, or systems 100 (or 100', 100'', or 100'''), 200 (or 200'), 300 (or 300'), 400 (or 400'), 500 (or 500'), and 600a-600e of FIGS. 1, 2, 3, 4, 5, and 6 can each also operate according to other modes of operation.

In the non-limiting embodiment of FIG. 10, method 1000, at block 1005, may comprise providing a first layer of vacuum sealable material. The first layer of vacuum sealable material may be formed from at least one of a flexible or rigid film, a flexible or rigid plastic, or foam, and/or the like. The first layer may be formed to be a thin sheet of material, a tray, and/or the like. Additionally, and/or alternatively, the first layer of vacuum sealable material may be made from liquid-impermeable material such as a film, a plastic, or other material that is liquid-impermeable.

At block 1010, the method 1000 may further comprise placing at least one absorbent pad on top of the first layer of vacuum sealable material. The absorbent pad may be at least one of a cloth, a sponge, a textured sponge, a square sponge, or a tubular sponge, and/or the like. Next, the method 1000, at block 1015, may comprise placing a solution on the absorbent pad, and the solution may be at least partially absorbed by the absorbent pad. The solution that is placed on the absorbent pad may be at least one of a cleaning solution, a detergent, a ready-to-use detergent, a concentrated detergent, a ready-to-use enzymatic detergent, a concentrated enzymatic detergent, water, distilled water, desalinated water, sterilized water, deionized water, sterilized distilled water, sterilized desalinated water, or sterilized deionized water, and/or the like.

Additionally, and/or alternatively, the method 1000, at block 1020, may comprise placing a second layer of vacuum sealable material over the first layer of vacuum sealable material, the at least one absorbent pad, and the solution. The second layer of vacuum sealable material may be formed from at least one of a flexible or rigid film, a flexible or rigid plastic, or foam, and/or the like. Additionally, and/or alternatively, the second layer of vacuum sealable material may be made from liquid-impermeable material such as a film, a plastic, or other material that is liquid-impermeable. Next, at least one chamber may be created with the first layer of vacuum sealable material and the second layer of vacuum sealable material, and each chamber may contain the at least one absorbent pad and the solution (block 1025).

Once the at least one chamber is created, the method 1000, at block 1030, may comprise evacuating air from the bag to create a partial vacuum seal surrounding the at least one absorbent pad and the solution contained within the bag. By at least partially evacuating air from the at least one chamber, the size of the chamber containing the at least one absorbent pad and the solution may be reduced.

The chambers containing the absorbent pad and solution may be placed in an outer bag containing other components for a medical kit. The other components of the medical kit may comprise one of one or more pairs of gloves, a transport bag, lubricating jelly, one or more syringes, tubing, one or more sets of bite blocks, one or more suction tips, one or more face masks, one or more nasal cannulas, one or more electrodes, one or more tip guards, one or more brushes, gauze, biohazard stickers, one or more bags containing water, or one or more valves (e.g., one or more air/water valves, one or more suction valves, one or more biopsy valves), and/or the like. Additionally, and/or alternatively, each medical kit may have at least one of a plurality of pairs of gloves of different sizes, a plurality of transport bags of different sizes, a plurality of masks of different sizes, a plurality of nasal cannulas of different sizes, a plurality of tip guards of different sizes, or a plurality of brushes of different sizes, and/or the like.

The outer bag containing the chamber and at least one other component may be vacuum sealed to reduce the size of the outer bag. By evacuating the outer bag, the size of the outer bag may be reduced. Further, the components contained within the outer bag may be sterilized such that the components are available for immediate use when the outer bag is opened.

Additionally, the outer bag may be created using a method similar to the method described above for the chamber containing the absorbent pad and solution. In a non-limiting example, the chamber containing the absorbent pad and solution and an additional component of the medical kit may be placed between a first layer of vacuum sealable material and a second layer of vacuum sealable material. The first layer of vacuum sealable material and the second layer of vacuum sealable material may be used to encase the chamber containing the absorbent pad and solution and an additional component of the medical kit and create an outer chamber. The air from the outer chamber may then be evacuated to encase the chamber containing the absorbent pad and solution and an additional component of the medical kit.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware, and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A dispenser for dispensing medical kits, the dispenser comprising:

a container comprising a top, a bottom, and a body between the top and the bottom, wherein a plurality of medical kits are disposable within the body of the container, wherein each medical kit comprises at least one bag containing at least one absorbent pad and a solution, and wherein the bag is evacuated to form a vacuum seal surrounding the at least one absorbent pad and solution;

a lid attached to the top of the container; and an opening disposed near the bottom of the container, wherein the opening is configured to dispense at least one medical kit at a time from the bottom of the container.

2. The dispenser of claim 1, wherein at least one medical kit protrudes slightly from the opening of the container.

3. The dispenser of claim 2, wherein removing the at least one medical kit protruding from the opening of the container causes another at least one medical kit to protrude from the opening of the container.

4. The dispenser of claim 1, wherein the plurality of medical kits are removably attached together via perforations.

5. The dispenser of claim 4, wherein the bottom of the container is configured to break the perforations.

6. The dispenser of claim 1, wherein the bottom comprises at least four spring loaded tabs and a hand tab on either side of the body near the bottom, wherein the plurality of medical kits when disposed in the body are arranged such that the perforations are adjacent to the sides, wherein removing one of the at least one medical kit by pulling a non-perforated side of the medical kit via one of the hand tabs causes the spring loaded tabs to flex and rebound to prevent the next medical kit from falling, wherein the resultant hanging medical kit can be removed by tearing along the perforations.

7. The dispenser of claim 1, wherein the bottom portion of the container is slanted.

8. The dispenser of claim 1, wherein gravity is used to aid dispensing of each medical kit from the container.

9. The dispenser of claim 1, wherein the lid is hingedly connected to the top of the container.

10. The dispenser of claim 1, wherein the container contains a predetermined amount of medical kits.

* * * * *